(12) United States Patent
Munk et al.

(10) Patent No.: US 10,808,530 B1
(45) Date of Patent: Oct. 20, 2020

(54) MINERAL ISOTOPES IN WATER, METHODS AND USES THEREOF

(71) Applicants: Lee Ann Munk, Eagle River, AK (US); Ryan Mathur, Huntington, PA (US)

(72) Inventors: Lee Ann Munk, Eagle River, AK (US); Ryan Mathur, Huntington, PA (US)

(73) Assignee: University of Alaska, Anchorage, Anchorage, AK (US)

( * ) Notice: Subject to any disclaimer, the term of this patent is extended or adjusted under 35 U.S.C. 154(b) by 539 days.

(21) Appl. No.: 13/960,549

(22) Filed: Aug. 6, 2013

Related U.S. Application Data

(60) Provisional application No. 61/680,660, filed on Aug. 7, 2012.

(51) Int. Cl.
| | | |
|---|---|---|
| *E21B 49/08* | (2006.01) | |
| *E21C 41/00* | (2006.01) | |
| *G01N 33/18* | (2006.01) | |

(52) U.S. Cl.
CPC .............. *E21B 49/08* (2013.01); *E21C 41/14* (2013.01); *G01N 33/18* (2013.01)

(58) Field of Classification Search
CPC .......... E21B 49/08; E21C 41/14; G01N 33/18
USPC ........................................................ 73/61.42
See application file for complete search history.

(56) References Cited

U.S. PATENT DOCUMENTS

| | | | | | |
|---|---|---|---|---|---|
| 2,330,026 | A | * | 9/1943 | Blau ...................... | G01V 9/007 256/36 |
| 2,470,401 | A | * | 5/1949 | Horvitz .................. | G01V 9/007 436/178 |
| 4,323,281 | A | * | 4/1982 | Greenwald, Sr. ....... | E21C 41/32 299/19 |
| 5,154,489 | A | * | 10/1992 | Lemieux ................. | E21C 41/26 299/18 |
| 5,310,248 | A | * | 5/1994 | King ....................... | E21C 35/24 299/1.1 |
| 5,646,863 | A | * | 7/1997 | Morton ................... | G01N 33/18 210/688 |
| 5,979,228 | A | * | 11/1999 | Smith .................... | G01N 33/246 73/53.01 |
| 6,020,289 | A | * | 2/2000 | Dymond ................. | C09K 8/24 507/118 |
| 6,164,727 | A | * | 12/2000 | Kelly ...................... | E21B 43/28 166/268 |
| 8,497,678 | B2 | * | 7/2013 | Rudakov ................ | G01N 24/08 324/303 |
| 9,664,010 | B2 | * | 5/2017 | Busche ................... | E21B 41/00 |
| 2009/0142137 | A1 | * | 6/2009 | Michailuck .............. | B09C 1/00 405/128.7 |
| 2011/0179888 | A1 | * | 7/2011 | Danesh .................... | G01N 1/08 73/864.44 |

OTHER PUBLICATIONS

David M. Borrok et al., Isotopic variations of dissolved copper and zinc in stream waters affected by historical mining, Geochimica et Cosmochimica Acta 72 (2008) 329-344.*

(Continued)

*Primary Examiner* — Marrit Eyassu
(74) *Attorney, Agent, or Firm* — Ballard Spahr LLP

(57) ABSTRACT

Disclosed herein are methods of measuring dissolved mineral isotopes, and other methods related thereto. This abstract is intended as a scanning tool for purposes of searching in the particular art and is not intended to be limiting of the present invention.

20 Claims, 14 Drawing Sheets

(56) References Cited

OTHER PUBLICATIONS

Ryan Mathur et al., Exploration potential of Cu isotope fractionation in porphyry copper deposits, Journal of Geochemical Exploration 102 (2009) 1-6.*

Weiqiang Li et al., Copper isotopic zonation in the Northparkes porphyry Cu—Au deposit, SE Australia, Geochimica et Cosmochimica Acta 74 (2010) 4078-4096.*

X.K. Zhu et al., Determination of natural Cu-isotope variation by plasma-source mass spectrometry: implications for use as geochemical tracers, Chemical Geology 163 (2000) 139-149.*

K.S. Smith, Approach for Environmental Baseline Water Sampling, Feb. 27-Mar. 2, 2011, US Geological Survey, Denver, CO, SME Annual Meeting, Preprint 11-157.*

Sarah Hurst, Mining News: Alaska's abandoned copper mines leave a mark, Sep. 25, 2005, Petroleum News, Mining News.*

Falko Wagner et al., The Bottom Sampler—a new technique for sampling bed sediments in streams and lakes, Jan. 7, 2002, Kluwer Academic Publishers, Hydrobiologia 505:73-76.*

Archer, C., et al. Mass discrimination correction in multiple-collector plasma source mass spectrometry: an example using Cu and Zn isotopes. Journal of Analytical Atomic Spectrometry, v. 19, pp. 656-665 (2004).

Asael, D., et al. Copper isotope fractionation in sedimentary copper mineralization (Timna Valley, Israel). Chemical Geology, v. 243, pp. 238-254 (2007).

Asael, D., et al. Fluid speciation controls of low temperature copper isotope fractionation applied to the Kupferschiefer and Timna ore deposits. Chemical Geology, v. 262, pp. 147-158 (2009).

Balisterieri, L.S., et al. Fractionation of Cu and Zn isotopes during adsorption onto amorphous Fe(III) oxyhydroxide: Experimental mixing of acid rock drainage and ambient river water. Geochimica et Cosmochimica Acta, v. 72(2), pp. 311-328 (2008).

Bermin, J., et al. The determination of the isotopic composition of Cu and Zn in sea water. Chemical Geology, v. 226(3-4), pp. 280-297 (2006).

Bigalke, M., et al. Stable Cu isotope fractionation in soils during oxic weathering and podzolization. Geochimica et Cosmochimica Acta, v. 75(11), pp. 3119-3134 (2011).

Bigalke, M., et al. Stable copper isotopes: A novel tool to trace copper behavior in hydromorphic soils. Soil Sci. Soc. Am. Journal, v. 74(1), pp. 60-73 (2009).

Bigalke, M., et al. Stable Cu and Zn isotope ratios as tracers of sources and transport of Cu and Zn in contaminated soil. Geochimica et Cosmochimica Acta, v. 74(23), pp. 6801-6813 (2010).

Borrok, D.M., et al. Isotopic variations of dissolved copper and zinc in stream waters affected by historical mining. Geochimica et Cosmochimica Acta, v. 72(2), pp. 329-344 (2008).

Eppinger, R.G., et al. An exploration hydrogeochemcial study at the Giant Pebble porphyry Cu—Au—Mo deposit, Alaska, USA, using high resolution ICP-MS. Economic Geology, v. 12(3), pp. 211-226, (Aug. 2012).

Fernandez, A., et al. Fractionation of Cu, Fe, and Zn isotopes during the oxidative weathering of sulfide-rich rocks. Chemical Geology, v. 264, pp. 1-12 (2009).

Graham, S., et al. Tracing Cu and Fe from source to porphyry; in situ determination of Cu and Fe isotope ratios in sulfides from the Grasberg Cu—Au deposit. Chemical Geology, v. 207(3-4), pp. 147-169 (2004).

Gregory, M.J., et al. Geometallurgy of the Pebble Porphyry Copper-Gold-Molybdenum deposit, Alaska: implications for gold distribution and paragenesis. Economic Geology, v. 108(3), pp. 463-482 (2013).

Haest, M., et al. Cu isotope variations in the Dikulushi Cu—Ag deposit, DRC: of primary origin or induced by supergene reworking? Economic Geology, v. 104, pp. 1055-1064 (2009).

Ikehata, K., et al. Copper isotope characteristics of copper-rich minerals from besshi-type volcanogenic massive sulfide deposits, Japan, determined using a femtosecond LA-MC-ICP-MS. Economic Geology, v. 106(2), pp. 307-316 (2011).

Kimball, B.E., et al. Copper isotope fractionation in acid mine drainage. Geochimica et Cosmochimica Acta, v. 73, pp. 1247-1263 (2009).

Lang, J.R., et al. Geology and magmatic-hydrothermal evolution of the Giant Pebble Porphyry Copper-Gold-Molybdenum deposit, Southwest Alaska, USA. Economic Geology, v. 108(3), pp. 437-462 (2013).

Larson, P.B., et al. Copper isotope ratios in magmatic and hydrothermal ore-forming environments. Chemical Geology, v. 201, pp. 337-350 (2003).

Li W., et al. The Cu isotopic signature of granites from the Lacklan Fold Belt, SE Australia. Chemical Geology, v. 258(1-2), pp. 38-49 (2009).

Li, W., et al. Copper isotopic zonation in the Nortparkes porphyry Cu—Au deposit, SE Australia. Geochimica et Cosmochimica Acta, v. 74(14), pp. 4078-4096 (2010).

Maher, K.C., et al. Experimental evaluation of the fluid-mineral fractionation of Cu isotopes at 250° C. and 300° C. Chemical Geology, v. 286(3-4), pp. 229-239 (2011).

Maher, K.C., et al. Variation in copper isotope ratios and controls on fractionation in hypogene skarn mineralization at Coroccohuayco and Tintaya, Peru. Economic Geology, v. 102(2), pp. 225-237 (2007).

Marechal, C.N., et al. Precise analysis of copper and zinc isotopic compositions by plasma-source mass spectrometry. Chemical Geology, v. 156(1-4), pp. 251-273 (1999).

Mathur, R., et al. Patterns in the Copper Isotope Composition of minerals in porphyry copper deposits in Southwestern United States. Econmic Geology, v. 105(8), pp. 1457-1467 (2010).

Mathur, R., et al. Cu isotopic fractionation in the supergene environment with and without bactera. Geochimica et Cosmochimica Acta, v. 69, pp. 5233-5246 (2005).

Mathur, R., et al. Exploration potential of Cu isotope fractionation in porphyry copper deposits. Journal of Geochemical Exploration, v. 102, pp. 1-6 (2009).

Mathur, R., et al. Identification of the dominant Cu ore minerals providing soluble copper at Canariaco, Peru through Cu isotope analyses of batch leach experiments. Hydrometallurgy, v. 101, pp. 15-19 (2010).

Mirnejad, H., et al. A comparative copper isotope study of porphyry copper deposits in Iran. Geochemistry—Exploration, Environment, Analysis, v. 10(4), pp. 413-418 (2010).

Palacios, C., et al. Pleistocene recycling of copper at a porphyry system, Atacama Desert, Chile: Cu isotope evidence. Mineralium Deposita, v. 46(1), pp. 1-7 (2011).

Pokrovsky, O.S., et al. Copper isotope fractionation during its interaction with soil and aquatic microorganisms and metal oxy(hydr)oxides; possible structural control. Geochimica et Cosmochimica Acta, v. 72(7), pp. 1742-1757 (2008).

Pribil, M.J., et al. Influence of sulfur-bearing polyatomic species on high precision measurements of Cu isotopic composition. Chemical Geology, v. 272(104), pp. 49-54 (2010).

Seo, J.H., et al. Quantum chemical calculations of equilibrium copper (I) isotope fractionations in ore-forming fluids. Chemical Geology, v. 243(3-4), pp. 225-237 (2007).

Vance, D., et al. The copper isotope geochemistry of rivers and the oceans. Earth and Planetary Science Letters, v. 274(1-2), pp. 204-213 (2008).

Wall, A.J., et al. Copper isotope fractionation during the oxidative phase transition of sulfide minerals, chalcocite to covellite, using time-resolved synchrotron X-ray diffraction. Abstracts with Programs—Geological Society of America, v. 38, pp. 432 (2006).

Wall, A.J., et al. A flow-through reaction cell that couples time-resolved X-ray diffraction with stable isotope analysis. Journal of Applied Crystallography, v. 44(2), pp. 429-432 (2011a).

Wall, A.J., et al. Cu isotope fractionation during bornite dissolution: an in situ X-ray diffraction analysis. Ore Geology Reviews, v. 42(1), pp. 62-70 (2011 b).

(56) References Cited

OTHER PUBLICATIONS

Zhu, X.K., et al. Determination of natural Cu-isotope variation by plasma-source mass spectrometry; implications for use as geochemical tracers. Chemical Geology, v. 163(1-4), pp. 139-149 (2000).

Zhu, X.K., et al. Mass fractionation processes of transition metal isotopes. Earth and Planetary Science Letters, v. 200(1-2), pp. 47-62 (2002).

* cited by examiner

MINERAL ISOTOPES IN WATER, METHODS AND USES THEREOF

CROSS-REFERENCE TO RELATED APPLICATIONS

This Application claims the benefit of U.S. Provisional Application No. 61/680,660, filed on Aug. 7, 2012, which is incorporated herein by reference in its entirety.

BACKGROUND

Current chemical exploration methods focus on determining the total mineral concentration, such as the total Cu concentration, in water, sediment, soil and rock to help guide where there are Cu anomalies that may be of economic interest. The most relied upon technique is hard rock drilling into an area that is determined to have good potential based on the sample types listed above as well as using geophysical methods to determine where metal exists (targets) in the Earth's crust. Drilling can costs millions of dollars and can be difficult to prohibitive in some areas where metallic ore deposits are expected to exist.

Thus, there exists a need for cheaper effective means to test where metals or minerals can be found. Accordingly, the methods disclosed herein provide tools to determine where metal exists (targets) in the Earth's crust. Specifically, methods of analyzing natural water for mineral isotope profiles are disclosed herein.

SUMMARY OF THE INVENTION

In accordance with the purpose(s) of the invention, as embodied and broadly described herein, the invention, in one aspect, relate to measurements of mineral isotopes in natural water samples and their use to locate mineral deposits.

The cost to perform the methods disclosed is cheaper than other geological tests to determine whether an area of interest contains a mineral ore. The disclosed methods only require collecting a natural water sample from the area of interest in the field. The mineral or mineral ore of interest can be copper (Cu).

Disclosed herein are methods of measuring dissolved mineral isotopes comprising simultaneously measuring two or more dissolved mineral isotopes in a natural water sample, wherein the dissolved mineral isotopes are from the same type of mineral. By measuring the dissolved mineral isotopes simultaneously one obtains accurate and reliable results of the distribution of the isotopes in the natural water sample.

In one aspect, the methods can simultaneously measure two dissolved mineral isotopes. The mineral isotopes can be stable isotopes in nature. For example, the mineral isotopes can comprises $^{65}Cu$ and $^{63}Cu$ for the element Cu.

In one aspect, the methods further comprise providing isotope measurements of a natural water sample, and a standard sample. The standard sample can be a NIST standard, for example a NIST 976 standard.

In one aspect, the methods can be performed by a mass spectrometer. Suitable mass spectrometers include, but are not limited to, induced coupled plasma multicollector mass spectrometers.

In one aspect, the natural water sample can be a sample from shallow natural water, such as a spring, stream, seep, pond, or lake.

In one aspect, the natural water sample can be taken from an area of interest. The area of interest can be an area where one wants to find out whether or not a mineral ore exist.

In one aspect, the methods can further comprise determining the $\delta^{isotope1}$mineral‰.

In another aspect the method can further comprise determining the range of $\delta^{isotope\ 1}$mineral‰ in one or more samples from an area of interest.

In another aspect, the average $\delta^{isotope1}$mineral‰ can indicate whether further tests to determine if a mineral ore exist are suitable.

Also disclosed herein, is a method of determining a mineral mining site comprising receiving a range of $\delta^{isotope}$ $_1$mineral values from an area of interest and performing further tests for minerals in the area of interest.

DETAILED DESCRIPTION

Figure 1:
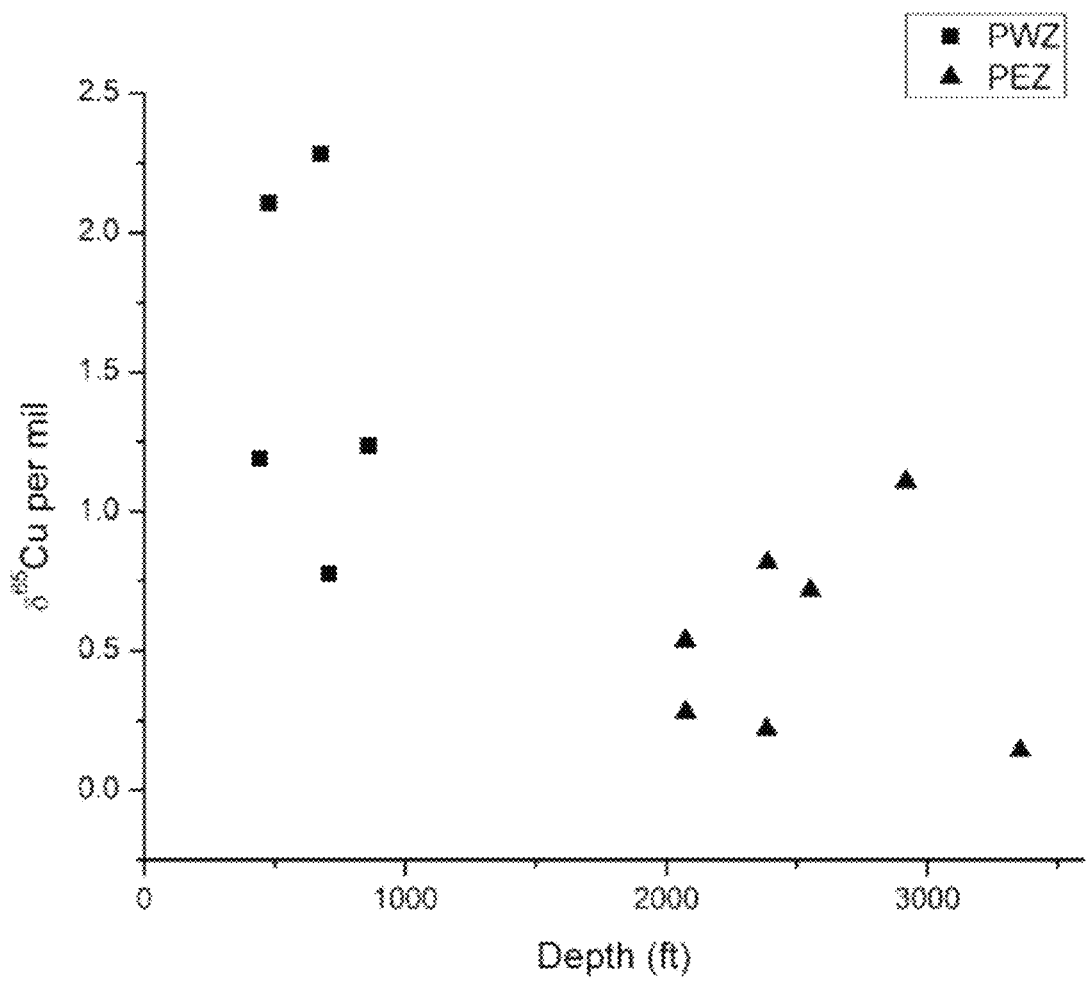
FIG. 1 shows the variation in $\delta^{65}Cu$ of hypogene mineralization with depth in the Pebble West Zone (PWZ) and Pebble East Zone (PEZ).

The present invention can be understood more readily by reference to the following detailed description of the invention and the Examples included therein.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

1. DEFINITIONS

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

The term "$\delta^{isotope1}mineral‰$" and the like terms, relates to dissolved mineral in a sample and can be expressed as "$\delta^{isotope1}mineral‰ = (((^{isotope\ 1}mineral_{sample}/^{isotope\ 2}mineral_{sample})/(^{isotope\ 1}mineral_{standard}/^{isotope\ 2}mineral_{standard})) - 1) \times 1000$. The $^{isotope\ 1}mineral$ is the same type of isotope in both the sample and the standard. The $^{isotope\ 2}mineral$ is the same type of isotope in both the sample and the standard. Both $^{isotope\ 1}mineral$ and $^{isotope\ 2}mineral$ are stable isotopes in nature. In one aspect, $^{isotope\ 1}mineral$ can be the most abundant isotope in nature. In another aspect, $^{isotope\ 2}mineral$ can be the most abundant isotope in nature. In another aspect, neither $^{isotope\ 1}mineral$ nor $^{isotope\ 2}mineral$ is the most abundant isotope found in nature for a mineral. A non-limiting example of $^{isotope\ 1}mineral$ is $^{65}Cu$. A non-limiting example of $^{isotope\ 2}mineral$ is $^{63}Cu$. Thus, when $^{isotope\ 1}mineral$ is $^{65}Cu$ and $^{isotope\ 2}mineral$ is $^{63}Cu$ the $\delta^{isotope\ 1}mineral‰$ is expressed as $\delta^{65}Cu‰ = (((^{65}Cu/^{63}Cu_{sample})/(^{65}Cu/^{63}Cu_{standard})) - 1) \times 1000$. An average $\delta^{65}Cu‰$ value refers to one value from one sample.

The term "natural water" or the like terms refer to water that originates from beneath the earths surface, for example, in soil pore spaces or in the fractures of rock formations. Natural water includes shallow natural water and, thus, includes seeps, streams, springs, ponds and lakes. In one aspect, the natural water can be ground water.

Disclosed are the components to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

2. METHODS

The cost to perform the methods disclosed is cheaper than other geological tests to determine whether an area of interest contains a mineral ore. The disclosed methods only require collecting a natural water sample from the area of interest in the field. The mineral of interest could be copper (Cu). Therefore, in areas with a concealed Cu deposit that have water available above them for sampling, the disclosed methods are efficient and effective ways of narrowing down the location of these types of deposits. Used in conjunction with the broad abilities of geophysics, the disclosed methods are most likely to be the most cost effective way to find Cu mineralization. The methods provide specific results which reveals where the Cu in the surface and shallow natural water is derived from. Thus, the results indicate whether a copper deposit exist and also if the deposit is hypogene or supergene. The only other way to determine this is to drill out a suspected deposit which costs millions of dollars and is not as precise because each drill hole only provides a directed window into the subsurface whereas using the disclosed methods. On the other hand, determining the Cu isotope distribution, from natural water is an order of magnitude less expensive and can be done by simply collecting sample from the natural water source. Thus, the disclosed methods are useful in help determining areas that could be suitable for mining or for further testing. The methods provide reliable values where one can determine whether or not further testing of the area is useful. Ultimately, the methods help to determine the location or mineral ores, such as copper ores, suitable for mining.

The methods determine the isotope distribution in various areas and are useful to provide reliable results for geochemical exploration. In one aspect, the mineral isotope distribution can be a copper isotope distribution such as the distribution of $^{65}Cu$ and $^{63}Cu$.

Disclosed herein are methods of measuring mineral isotopes comprising simultaneously measuring two or more dissolved mineral isotopes in a natural water sample, wherein the dissolved mineral isotopes are from the same type of mineral. By measuring the dissolved mineral isotopes simultaneously one get accurate and reliable results of the distribution of the isotopes in the natural water sample. Thus, the instrument, for example a mass spectrometer, at the same in the same natural water sample analyses the sample for the two dissolved mineral isotopes. This provides reliable results in term of the ratio of the isotopes in the sample. Two separate measurements of the two isotopes would not provide reliable and meaningful results in terms of the ratio of the isotopes in the sample.

In one aspect, the methods can simultaneously measure two dissolved mineral isotopes. The mineral isotopes can be stable isotopes in nature. For example, the dissolved mineral isotopes can comprises $^{65}Cu$ and $^{63}Cu$. Other suitable minerals with two or more isotopes that can be measured simultaneously include, but are not limited to, Fe, Mo, Zn and any other transition metal.

In one aspect, the methods further comprise providing a natural water sample. In one aspect, the methods further comprise providing a standard sample. In one aspect, the methods further comprise providing a natural water sample, and a standard sample. The standard sample can be a NIST standard, for example NIST 976 standard.

In one aspect, the methods can be performed by a mass spectrometer. Suitable mass spectrometers include, but are not limited to, ICP-MS multicollectors of thermal ionization mass spectrometers.

In one aspect, the natural water sample can be a sample from shallow natural water. In another aspect, the natural water sample can be a sample from a spring, stream or seep. For example, the natural water sample can be a sample from a spring. In another example, the natural water sample can be a sample from a seep. In another example, the natural water sample can be a sample from a stream. In another example, the natural water sample can be a sample from a pond. In another example, the natural water sample can be a sample from a lake.

In one aspect, the natural water sample can be taken from an area of interest. The area of interest can be an area where the one wants to find out whether or not a mineral ore exist. In one aspect, there could have been previous indications that a mineral ore existed in the area of interest, for example a copper ore. In another aspect, the natural water sample can be the first sample taken to indicate whether or not a mineral ore exist in the area of interest, such as a copper ore.

In one aspect, an area of interest can have a size of at least 100 kilometer$^2$ (km$^2$), 50 km$^2$, 25 km$^2$, 10 km$^2$, 5 km$^2$ or 1 km$^2$. In one aspect, an area of interest can have a size of at most 100 kilometer$^2$ (km$^2$), 50 km$^2$, 25 km$^2$, 10 km$^2$, 5 km$^2$ or 1 km$^2$. In one aspect, an area of interest can have a size of between 100-50 kilometer$^2$ (km$^2$), 50-25 km$^2$, 25-10 km$^2$, 10-5 km$^2$, 5-1 km$^2$ or 1-0 km$^2$. In one aspect, the area of interest can comprise a pebble deposit. In one aspect, an area of interest can comprise natural water.

In one aspect, the methods can be performed multiple times. For example, the methods can be performed multiple times using the same natural water sample. The average result of those measurements can be calculated.

In one aspect, the methods can further comprise determining the $\delta^{isotope\ 1}$mineral‰.

In another aspect the method can further comprise determining the $\delta^{isotope\ 1}$mineral‰ in one or more samples from an area of interest. In one aspect, the $\delta^{isotope\ 1}$mineral‰ can indicate whether further tests to determine if an ore exists in the subsurface. In one aspect the $\delta^{isotope\ 1}$mineral‰ can be the $\delta^{65}Cu$‰. The $\delta^{isotope\ 1}$mineral‰ can indicate whether or not a mineral ore exist. A $\delta^{isotope\ 1}$mineral‰ above 0.5‰, 1.0‰, 1.5‰, 2.0‰ or 2.5‰. For example, a hypogene zone exists when the $\delta^{65}Cu$‰ is above 1.5‰. In one aspect, the $\delta^{isotope\ 1}$mineral‰ values can be the average $\delta^{isotope\ 1}$mineral‰.

Also disclosed herein, is a method of determining a mineral mining site comprising receiving a range of $\delta^{isotope\ 1}$mineral values from an area of interest and performing mining activities in the area of interest. In one aspect, the performing mining activities can be mining. In another aspect, performing mining activities can be performing further tests. Suitable tests include, but are not limited to, test drilling, geographical surveys and geochemical soil and water sampling. In one aspect, the mineral is copper. In one aspect, the $\delta^{isotope\ 1}$mineral values can be obtained by the methods described herein.

Also disclosed herein is a method of identifying a mineral ore comprising a) providing a natural water sample from an area of interest; b) simultaneously measuring two or more mineral isotopes in the natural water sample, wherein the mineral isotopes are from the same type of mineral; and c) determining the range of $\delta^{isotope\ 1}$mineral.

In one aspect, the mineral ore is a copper ore. For example, the mineral can be copper. In one aspect, the $\delta^{isotope\ 1}$mineral can be $\delta^{65}Cu$‰. In one aspect, the $\delta^{isotope\ 1}$mineral values can be more than 0.5‰, 1.0‰, 1.5‰, 2.0‰ or 2.5‰.

In one aspect, the method further comprises mining the area of interest for a mineral. The mineral can be copper. The mining can be for copper. The mining can extract the same mineral that was measured simultaneously.

3. EXAMPLES

(a) Example 1—Methods of Detecting Concealed Ore Deposits Such as the Pebble Cu—Au—Mo Porphyry Deposit The fractionation of Cu isotopes in primary and secondary mineralization associated with porphyry systems has been used to vector to deposits and to understand environmental signatures of Cu-bearing waste rock (Asael et al., 2007; Asael et al., 2009; Haest et al., 2009; Kimball et al., 2009; Larson et al., 2003; Maher and Larson, 2007; Mathur et al., 2005; Mathur and Schlitt, 2010; Mathur et al., 2009; Wall et al., 2006). This study at the Pebble deposit was performed to understand the distribution of Cu isotopes in different mineralized zones as well as in surface and shallow natural water (seeps). The results indicate that the Cu isotope signature of easily accessible water (seeps) in the area of the Pebble deposit can be used to identify mineralization concealed below extensive glacial sediments and post-hydrothermal cover rocks.

Figure 2:
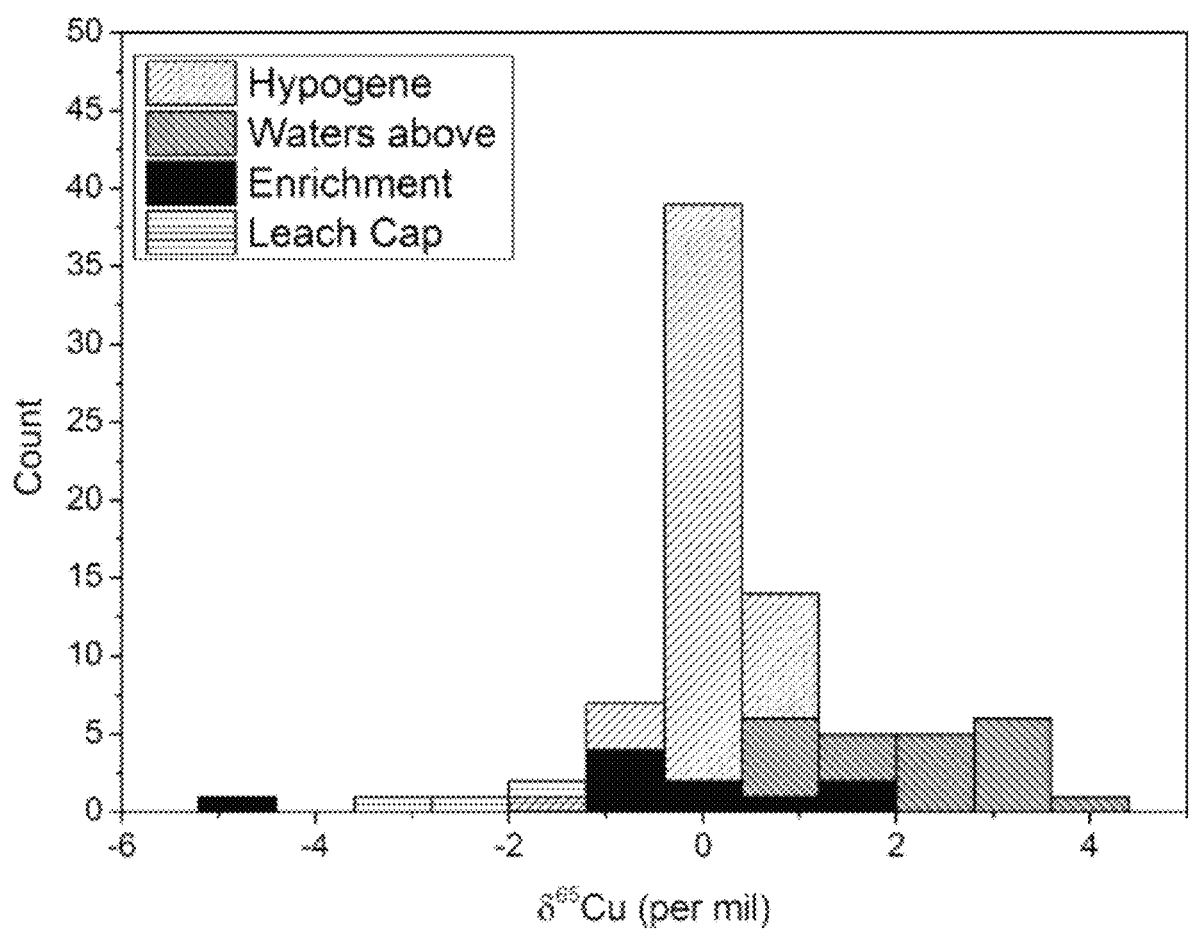
FIG. 2 shows the Cu isotope composition of solids (hypogene, enrichment (supergene), leach cap) and waters above the Pebble Deposit.

The general trend of Cu isotope signatures in porphyry deposits studied thus far (Mathur et al., 2011) is that the $\delta^{65}Cu$ of the leach cap minerals<hypogene minerals<supergene enrichment minerals. As shown herein, the Cu isotope signature of the hypogene, supergene and leach caps have distinct ranges of $\delta^{65}Cu$ values with high temperature deposits displaying a narrower range of values than low temperature deposits [where $\delta^{65}Cu‰= (^{65}Cu/^{63}Cu_{sample}/^{65}Cu/^{63}Cu_{NIST\ 976\ standard})-1)*10^3$]. In the Pebble deposit, sulfide mineral $\delta^{65}Cu$ values range from 0.78‰ to 2.28‰ (hypogene West Zone), 0.02‰ to 1.55‰ (hypogene East Zone), −3.49‰ to 1.88‰ (oxide West Zone), and −5.04‰ to 1.27‰ (supergene West Zone). The $\delta^{65}Cu$ signature of hypogene mineralization shows a relationship to elevation within the deposit (FIG. 1), whereas laterally the $\delta^{65}Cu$ values become depleted farther from the hypogene source (FIG. 2).

The Cu isotope composition of stream and shallow natural water seeps above and lateral to the concealed Pebble deposit were also analyzed. The results indicate that the shallow natural waters are enriched in $\delta^{65}Cu$ above the deposit and, along with stream water, become progressively depleted in $^{65}Cu$ away from the deposit. This trend persists even in waters that have only ~1 µg/L dissolved Cu (FIG. 3), i.e., at an absolute concentration which would not by itself generate much interest during routine exploration targeting exercises. This indicates that the Cu isotope signature of the Pebble deposit is preserved in shallow groundwater seeps and that low cost (as compared to drilling) analyses of such easily accessible waters could be a very useful tool in exploration for Cu porphyry deposits in similar concealed settings. The copper isotope patterns in both minerals and surface waters demonstrate the potential use of copper isotope fractionation both for mineral exploration and to constrain potential sources of copper during baseline environmental studies.

(b) Example 2—Geologic Exploration Application of Cu Isotope Signatures of Ores and Surface Waters at the Pebble Au—Cu—Mo Porphyry Deposit, Alaska The Pebble Cu—Au—Mo porphyry deposit formed at about 90 Ma and is located in southwest Alaska. The total resource is 10.8 Gt which contains 80.6 Glb Cu, 5.6 Glb Mo and 107.4 Moz Au. Mineralization occurs in a West Zone exposed at surface and an East Zone concealed by Tertiary volcanics and younger glacial till. This study uses copper isotopes measured in minerals and surface waters to understand high temperature mineralization processes and current weathering processes. Sulfide minerals $\delta^{65}Cu$ values ranging from 0.78‰ to 2.28‰ (hypogene West), 0.02‰ to 1.55‰ (hypogene East), −3.49‰ to 1.88‰ (oxide West), and −5.04‰ to 1.27‰ (supergene West). The mineralization results show a relationship of the hypogene minerals to elevation whereas $\delta^{65}Cu$ values become depleted farther from the hypogene source. Shallow ground waters are enriched in $\delta^{65}Cu$ above the deposit and become progressively depleted in $^{65}Cu$ away from the deposit. Patterns measured in the copper isotope composition of both the minerals and surface waters demonstrate the potential use of copper isotope fractionation in exploration geology as well as to understand the copper sources to the environment.

Several copper isotope studies that have demonstrated the application of Cu isotope fractionation for the exploration geologic community (Asael et al. 2007; Asael et al. 2009; Haest et al. 2009; Kimball et al. 2009; Larson et al. 2003; Maher and Larson 2007; Mathur et al. 2005; Mathur and Schlitt 2010; Mathur et al. 2009; Wall et al. 2006). Here, Cu isotope fractionation was measured in minerals and aqueous solutions near the Pebble porphyry copper deposit. The aims of the study are to investigate whether or not Cu isotope data provides the ability to vector to hidden resources through using Cu isotope contour maps and to understand the degree of weathering and its relationship to the impact of supergene enrichment. A copper isotope measurement of the water could be used to identify which Cu minerals are weathering and/or used to vector to the source of weathering Cu minerals. Given that the Cu isotope compositions will be measured of many copper minerals; the copper isotopic composition of the water because the fractionation factors for chalcopyrite, chalcocite and enargite are distinctly different. In other words, when chalcopyrite chemically weathers the waters are 1.6 per mil heavier than the chalcopyrite whereas when chalcocite weathers the waters are 2.6 per mil heavier than the chalcocite. Therefore the isotopic composition of the waters provides insight into the minerals that are weathering. Additionally, mineral (sulphides, Fe-oxides derived from leaching of sulphides and found on rocks in association with waters) could be used in three manners:

a) ore minerals could be used to construct contour maps to vector to hypogene/supergene (or lateral motion as seen in exotic Cu deposits) sources.

b) water could be used to fingerprint mineralization zone and tie relationships between different ore bodies that could be separated by faults.

c) Fe-oxides and waters could indicate the transport and cycling of Cu derived from ore minerals.

Figure 4:
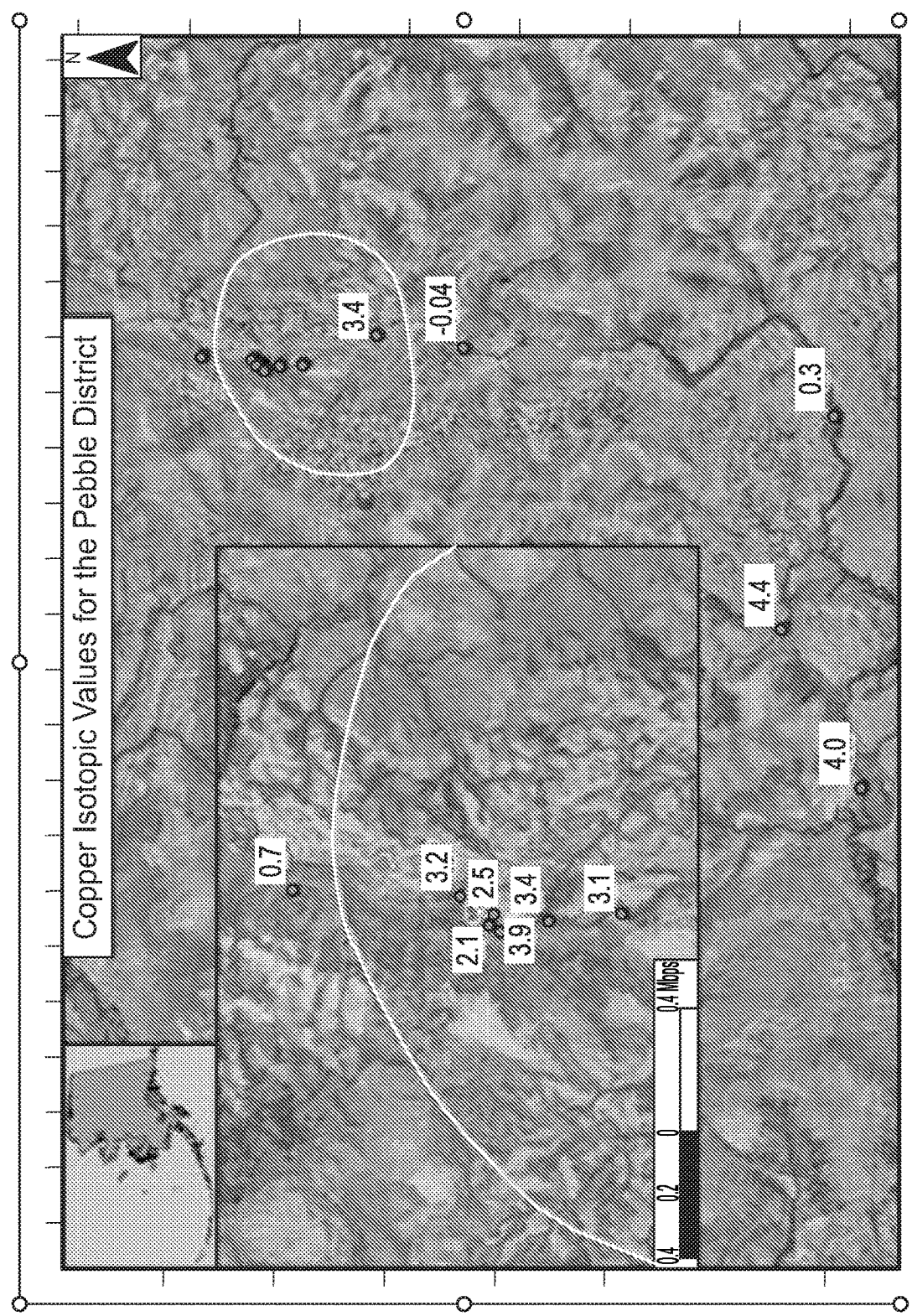
FIG. 4 shows the sample location map for waters analyzed. The circle outlines the deposit and the most enriched Cu isotope values occur within this zone and are in the window pane in the left of the Figure.

(c) Results and Discussion 6 seeps and 3 stream waters were collected and analyzed in two different time intervals (FIG. 4).

Figure 3:
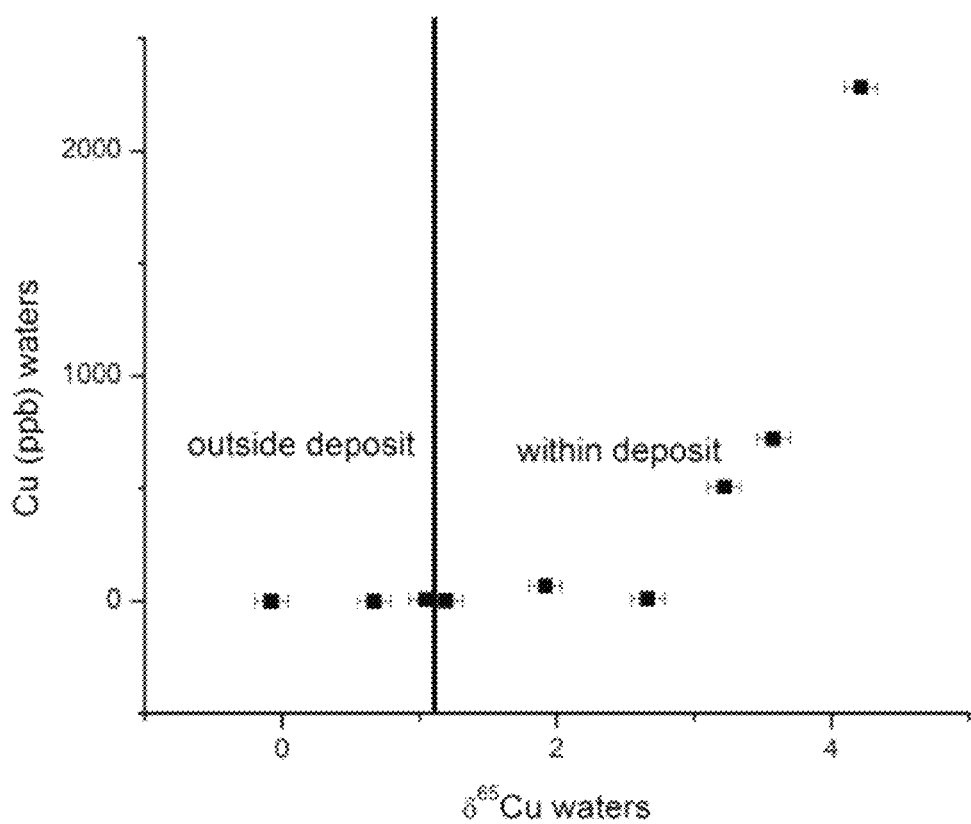
FIG. 3 shows the relationship of Cu concentration and $\delta^{65}Cu$ of shallow natural water seeps and streams within and outside the deposit area. Even at low (~1 µg/L) Cu concentrations the $\delta^{65}Cu$ signature still indicates whether or not the Cu is coming from sulfide mineralization.

The seeps directly on top of the deposit have isotopically enriched $\delta^{65}Cu$ signatures, indicating that there is active oxidative weathering of Cu-sulfide minerals as a source for Cu in these waters. Given the starting hypogene mineral Cu isotope compositions (on the average 1 per mil) and the seeps at 2.7 per mil, a fractionation factor of 1.5 or so is obtained. This fractionation factor is identical to chalcopyrite and could indicate that the weathering of chalcopyrite is the source of Cu in the waters from the seeps. Equally important is the observation that enriched (heavier isotope ratios) occurred in samples above the deposit that did not have elevated concentrations of Cu (FIG. 3). Thus, the isotope ratios provide evidence of weathering of copper minerals that is not detected with concentration measurements alone.

Figure 5:
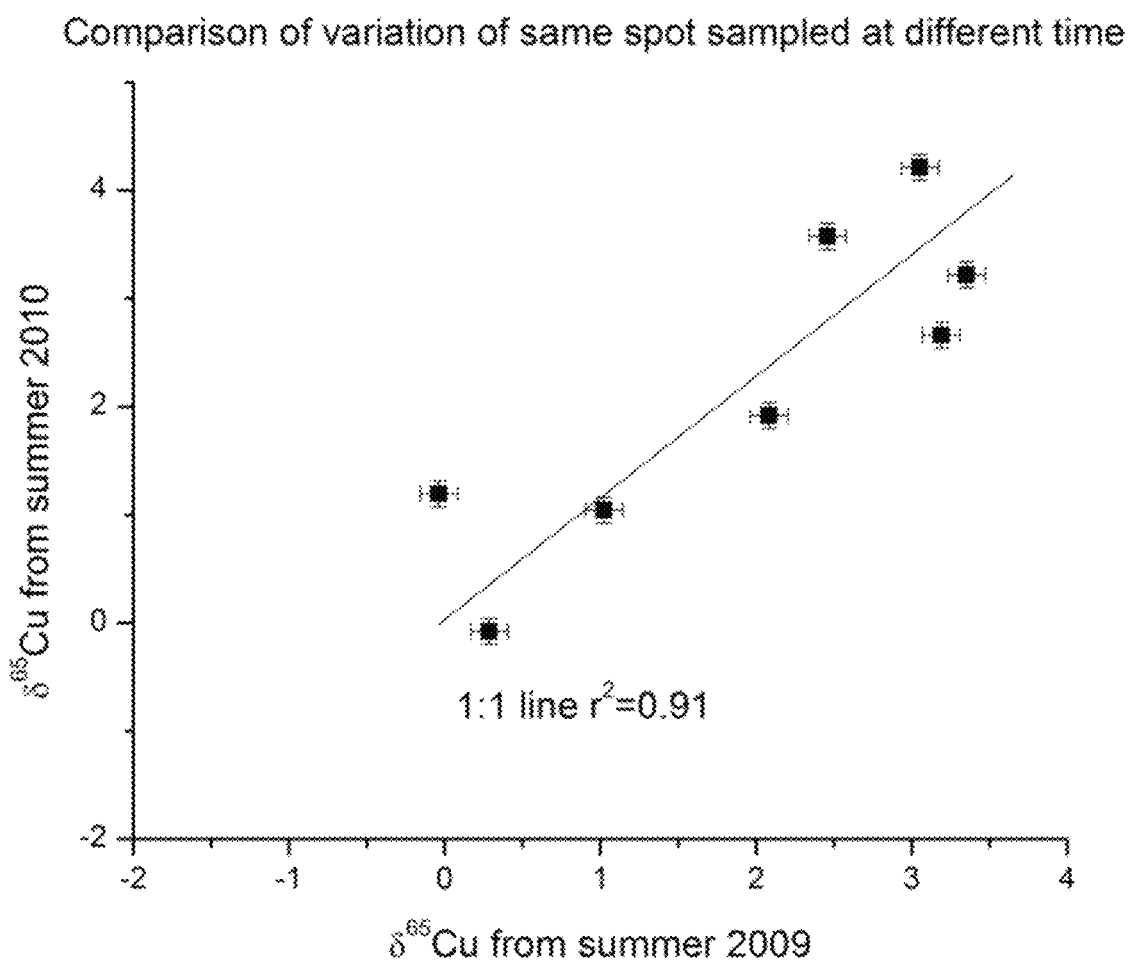
FIG. 5 indicates the measured Cu isotope ratios from the same location sampled at two distinct time intervals.

FIG. 5 illustrates copper isotope composition of the tested waters samples. The data fall within a slope that is 1.04 with $r^2=0.91$. This indicates that the signal of copper mineral weathering in the waters remains constant between the two days analyzed. Although there are only two time points, the relative consistency demonstrates the potential that the isotope ratios remain constant regardless of when sampled. If this relationship holds true over several seasons of sampling, the ability to use the isotope composition for exploration becomes significant along with the environmental ability to detect change once/if mining commences. Annual sampling and analysis will confirm this.

For the hypogene high temperature (>300° C.) mineralization Cu isotopes display a surprisingly large variation from 0.22 to 2.28‰. There is a distinct difference between the copper isotope compositions for minerals from drill core in the west (PWZ) in comparison to drill core minerals from the east (PWE) FIG. 1. Samples from PWZ are enriched in $^{65}$Cu compared to the minerals PEZ. This relationship exists without designating specific mineralogy. Assuming a bottom to top cycling of the high-temperature hydrothermal system, the Cu isotopes seemingly match this trend in that they show a progressive deposition of $^{65}$Cu farther from the porphyry center. This observation has profound exploration geologic impact because this pattern could potentially vector to the hypogene sources and allow for interpretation of location within the porphyry system. Of course, the property would have to be drilled and you would need to use drill cu sulfides in drill core, but the values could be used to assist in further defining the limits of mineralization in the area and where exploration should continue in the area.

In the supergene mineralization several relationships can be seen. One the average $\delta^{65}$Cu for hypogene minerals (0.89‰, n=12)>supergene enrichment (0.26‰, n=5)>leach cap (−1.2‰, n=8). The leach cap possess an isotopically deplete signature in comparison to the hypogene and supergene enrichment samples. This most likely indicates that $^{65}$Cu has been weathered through oxidation of the initial hypogene minerals. However, the $^{65}$Cu does not appear to be enriched in the supergene zone. This is in contrast to the copper isotopes measurements from minerals in porphyry copper deposits in the American Southwest. The chalcocite at Pebble does not possess enriched $^{65}$Cu isotope signatures. This implies that typical supergene processes where the Cu migrates vertically and is precipitated and was preserved either did not occur or are not preserved here. Rather the enrichment appears to be weathered and the weathered solutions that contained the enriched were not preserved in the mineralization analyzed here.

For the Fe-oxides found in association with the waters analyzed, the Cu isotope composition of the Fe-oxides were <waters> or =the hypogene sulfides. Several biological and inorganic redox mechanisms could be used to explain the signatures found for the Cu that is most absorbed on the surface of the Fe-oxides, but it appears that the secondary in-stream precipitates are not enriched in $^{65}$Cu.

(d) Example 3—Modern and Paleo-Fluid Pathways Revealed by Cu Isotope Fractionation in Surface Waters and Ores of the Pebble Porphyry Cu—Au—Mo Deposit, Alaska This study uses copper isotope ratios measured in minerals and shallow groundwater and surface waters to understand high-temperature mineralization and active weathering processes at the Pebble porphyry Cu—Au—Mo deposit, Alaska. The West Zone of the deposit contains hypogene mineralization with a supergene overprint, whereas the contiguous East Zone contains only hypogene mineralization. Sulfide-rich rock powders and mineral separates have $\delta^{65}$Cu values that range from 0.78‰ to 2.28‰ (hypogene West), 0.02‰ to 1.55‰ (hypogene East), −3.49‰ to 1.88‰ (oxide West), and −5.04‰ to 1.27‰ (supergene West). The results show a relationship between the hypogene mineral ratios and elevation in the deposit where $\delta^{65}$Cu increases with distance from the inferred source of hypogenefluids. The $\delta^{65}$Cu correlate with silicate alteration assemblages with positive values confined to the quartz-illite-pyrite, sericite, and pyrophyllite alteration zones and negative values confined to the potassic and sodic-potassic domains. This empirical evidence could indicate that fractionation of Cu isotopes is controlled by pH and/or temperature variations. Shallow surface waters show enriched $\delta^{65}$Cu above the deposit and become progressively depleted away from the deposit. Patterns measured in the copper isotope ratios of both minerals and surface waters demonstrate the potential use of copper isotope distribution in exploration geology as well as to understanding the sources of copper in the surface and near-surface environments.

The study described herein utilizes Cu isotope compositions in rocks, minerals, and water samples to further our understanding of how Cu isotope distribution can be used as a geochemical exploration tool. The application of Cu isotope fractionation is two-fold where high-temperature ore forming processes and low-temperature water-rock interactions that occur during weathering of Cu-sulfide-rich rocks are highlighted. The Pebble deposit presents an ideal location to use this isotope system because extensive drill core combined with well-constrained geologic relationships are available, and the composition of surface waters has not been impacted by active mining. The data herein shows how the $\delta^{65}$Cu signature can be used at various stages of exploration activity from basic surface exploration to more advanced drill core exploration.

With respect to high-temperature mineralization, three previous studies (Graham et al., 2004; Li et al., 2010; Maher and Larson, 2007) measured Cu isotope fractionation in porphyry systems like Pebble. Li et al. (2010) and Graham et al. (2004) found complicated Cu isotope spatial relationships with mineralization. Maher and Larson (2007) studied a skarn deposit and discovered that Cu minerals closer to the source of mineralization have lower $\delta^{65}$Cu compositions compared to those in distal mineralized parts of the deposit. Each study indicated the need for experimental work that could be used to predict the patterns seen in nature. To date, Seo et al. (2007) and Maher et at. (2011) provide theoretical and experimental data that demonstrate fractionation on the order of >1‰ can occur at high-temperatures. This study described herein expands the analyses of high-temperature $\delta^{65}$Cu signatures in Cu sulfides through increased sampling and contouring of data with the goal of using the $\delta^{65}$Cu to vector towards fluid pathways.

Many other studies (Balistrieri et al., 2008; Borrok et al., 2008; Fernandez and Borrok; Mathur et al., 2010; Mathur et al., 2005; Mathur and Schlitt, 2010; Mirnejad et al., 2010; Wall et al., 2011a; Wall et al., 2011b) have focused on the weathering of Cu minerals and the processes associated with supergene enrichment because the degree of fractionation is much greater in this environment. Copper isotope measurements of minerals formed during the supergene process provide insight into the weathering history of porphyry deposits (Haest et al., 2009; Mathur et al., 2010; Mathur et al., 2009; Mirnejad et al., 2010; Palacios et al., 2011). Large Cu isotope fractionation in the supergene environment has been previously recorded to provide insight into the weathering history.

Surficial low-temperature aqueous solutions are intimately connected with the weathering of the Pebble deposit. The Cu isotope ratios and concentrations in shallow ground waters (seeps) were analyzed in order to measure an isotopic fingerprint of actively-weathering Cu sulfides. The seeps provide insight to the active weathering processes because the waters migrated through and interacted with the tills and bedrock of the deposit. The oxidation of Cu-rich sulfide minerals produces waters that are isotopically enriched in the $^{65}$Cu isotope (Borrok et al., 2008; Kimball et al., 2009; Mathur et al., 2005) in comparison to the weathered sulfide mineral.

The utility of this relationship for exploration geologists is that the waters above the known Pebble deposit would possess this heavier Cu isotope signature (positive $\delta^{65}$Cu) in comparison to the other seep waters that are not actively weathering Cu-rich sulfides. The technique is useful in shallow surface hydrogeologic conditions and can be more complicated with lateral to sub-lateral fluid flow. This study demonstrates that spatial analysis of copper isotope measurements of minerals and waters can be used by exploration geologists to vector to or indicate the presence of mineralized rocks at depth.

(i) Geology and Hydrothermal Characteristics of the Pebble Deposit

The Pebble deposit comprises the contiguous West and East Zones (FIG. 6), which are interpreted as two coeval thermal and fluid centers in a single magmatic-hydrothermal system (Lang et al, this volume). The oldest rocks in the deposit are siltstones and lesser sandstones of the Jurassic-Cretaceous Kahiltna Flysch. The flysch was intruded by diorite and granodiorite sills at about 96 Ma, and in the West Zone, by a complex of 96 Ma alkalic intrusions and related diatreme and intrusion breccias (Lang et al., this volume). All of these units were subsequently intruded by hornblende granodiorite bodes of about 90 Ma which are genetically related to at least some stages of mineralization at Pebble. The 90 Ma intrusions comprise four small bodies in the West Zone along with the much larger East Zone pluton and recent drilling demonstrates that these bodies merge at depth. Re—Os isotopic ages molybdenite samples range from 89.5 to 90.4 Ma. The West Zone crops out at surface in one small rubble crop, whereas the East Zone is unconformably overlain by Late Cretaceous to Eocene sedimentary and volcanic strata. Both zones are covered by glacial sediments that are typically <30 meters thick (Lang et al, this volume).

Variations in hypogene grade and metal ratios reflect multiple stages of metal introduction and redistribution (Gregory, This volume; Lang, This volume). Early Cu—Au—Mo mineralization formed during one or more stages of widespread potassic and sodic-potassic alteration associated with multiple generations of quartz-sulfide veins. Sodic-potassic alteration dominates the western half of the deposit and comprises albite-K-feldspar-biotite with a pyrite-chalcopyrite sulfide assemblage. In the eastern part of the deposit, potassic alteration is dominated by K-feldspar, quartz and biotite and sulfides are mostly chalcopyrite accompanied by minor pyrite. This alteration is concentrated near the top of the East Zone pluton and in its immediate host rocks and with depth yields to a weakly mineralized sodic-potassic-calcic alteration (Gregory et al., this volume). Most of the gold in these alteration zones occurs as micro-inclusions in chalcopyrite and pyrite. A zone of quartz-illite-pyrite has been preserved along the western extension of the potassic alteration zone. This assemblage is interpreted to have originally formed as a cap to potassic alteration which overprinted the potassic alteration as the hydrothermal system cooled and collapsed. The Cu and Mo grades are lower in the quartz-illite-pyrite zone than surrounding alteration types, but Au grades are similar (Gregory et al., this volume).

Pervasive low-temperature illite and illite-kaolinite alteration respectively overprint the potassic and sodic-potassic assemblages throughout most of the deposit. Biotite is replaced by illite during illite alteration, whereas it is typically preserved in illite-kaolinite alteration. Igneous and/or hydrothermal quartz and K-feldspar are typically preserved in both assemblages. Minor pyrite also precipitated during both illite and illite-kaolinite alteration and copper and gold was variably redistributed. There is an apparent, but poorly defined, reduction in overall metal grade where the illite and illite-kaolinite alteration is most intense (Gregory et al., this volume).

Late advanced argillic alteration overprinted older sodic-potassic, potassic, and illite assemblages in the Pebble East Zone only (Gregory, This volume; Lang, This volume). The advanced argillic alteration assemblages consist of a core of quartz-pyrophyllite and an envelope of sericte alteration pyrophyllite-quartz-sericite alteration with high concentrations of pyrite and chalcopyrite. The sericite-rich alteration has a high-sulfidation assemblage of pyrite-bornite-digenite (±covellite±enargite). Mineralization related to advanced argillic alteration augmented the grades of both copper and gold precipitated during earlier alteration events and produced domains with the highest grades of copper and gold in the Pebble deposit (Gregory et al., this volume; Lang et al., this volume).

An alteration assemblage of quartz-illite-pyriteis preserved along the western extension of the potassic alteration domain in the upper-central part of the deposit. This assemblage is interpreted to represent a cap that telescoped onto potassic alteration as the system cooled. Areas affected by quartz-illite-pyrite alteration have lower Cu and Mo grades than surrounding alteration types but retain similar concentrations of Au. Late quartz-sericite-pyrite alteration, which is auriferous but which lacks Cu—Mo mineralization, forms a very wide halo to the deposit. Weakly auriferous propylitic alteration of uncertain timing only occurs well outside the Pebble deposit, outboard of the quartz-sericite-pyrite alteration. Supergene chalcocite and covellite partially replace hypogene chalcopyrite at the top of the West Zone. There is no evidence for paleo-supergene effects preserved below the younger cover rocks in the East Zone (Lang et al, this volume).

(ii) Methods and Sampling

Rock and mineral samples were obtained from 24 drill holes. Drill holes were selected based on the intersections with different silicate alteration types. Selection of samples from core was restricted to intervals with greater than 0.5% Cu grades to ensure that chalcopyrite was included. Because the leach cap and supergene enrichment is rare at the deposit, only eight samples from different holes were analyzed, the remaining samples did not possess supergene minerals.

Pure sulfide mineral samples hand-picked from veins or, in the case of disseminated sulfides, whole rock samples were chosen for analyses. Minerals and rocks were powdered and <400 micron powders were used for analysis. Phases in both minerals and powders were identified through powder X-ray diffraction and peaks were visually matched and identified.

Use of rock powders is non-ideal for interpreting Cu isotope compositions because multiple Cu bearing phases exist in the mixtures. Samples from certain intervals provided small portions of drill core with disseminated ore; therefore rock powders were the only option for analysis. To monitor the relative proportions of potential phases providing copper, Cu/Fe ratios measured from the samples are provided in Table 1. Higher Cu/Fe ratios indicate greater proportions of chalcopyrite and/or other Cu-rich minerals phases. Previous studies have demonstrated relatively homogenous Cu isotope compositions of micron-scale Cu isotope analyses of minerals compared to whole rock Cu isotope compositions (Ikehata et al., 2011).

Shallow groundwater was collected from seeps proximal and distal to the deposit and five samples were taken from nearby streams. Approximately 500 mL of water was collected from each site. The waters were filtered and acidified within five hours of collection. At 14 sites, water samples were collected from the same location three times over a 3-year interval to assess seasonal variations. At three sites, iron-oxide precipitates were forming on the base of seeps; these were collected by suction into plastic tubing and then stored in HDPE bottles. The precipitates were subsequently freeze-dried before digestion. Copper and Fe concentrations were measured by inductively coupled plasma mass spectrometry (ICP-MS) at the University of Alaska Anchorage ASET lab by a modified EPA 200.8 method.

Both mineral and rock powders were weighed (0.02 g for minerals and 0.10 g for rock powders) and dissolved in 4 ml of heated (80° C.) ultrapure aqua regia for at least 24 hours. Aliquots of each mineral and rock solution and the acidified waters were diluted 1000 fold for concentration analysis by ICP-MS at University of Alaska Anchorage. Concentrations of both Cu and Fe were monitored to ascertain the appropriate amount of ions to load onto the ion exchange resins. To avoid potential isobaric interference, ion exchange chromatography was conducted on all samples (Marechal et al., 1999; Pribil et al.; Zhu et al., 2000). The protocols for ion exchange chromatography for the solids and waters of the different solution matrices are outlined in (Kimball et al., 2009; Mathur et al., 2005; Mathur et al., 2009).

Samples were introduced into the ICP-MS multicollector (Isoprobe, at the University of Arizona) at approximately 200 μg/L in 2% ultra-pure nitric acid which produced between 1-3 V $^{63}$Cu signals. Mass bias was corrected by standard-sample-standard bracketing using the NIST 976 Cu standard. Analytical conditions are further discussed in Mathur et al. (2005) and Mathur et al. (2009). Samples were measured in duplicate, thus the reported ratio represents an average of two different analyses of the same solution at different times in the analytical session. The error of the analyses is most conservatively estimated by calculating the variation of a standard over multiple analytical sessions. The 26 error for the standard is 0.12 per mil (n=382). All sample duplicates fell within the reported error.

(iii) Results

Figure 7:
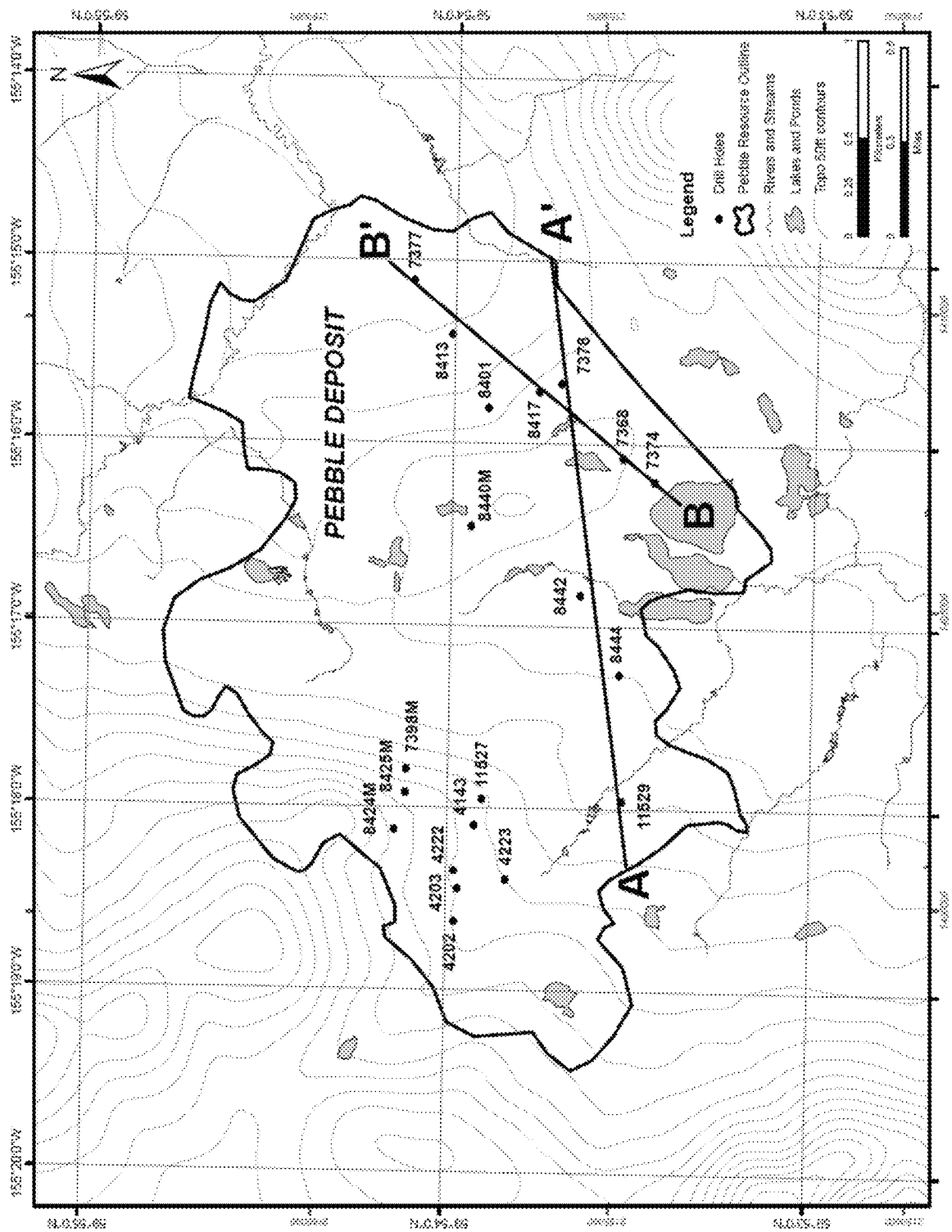
FIG. 7 shows the deposit-scale topographic map (eastings and northings indicated) with cross sections labeled. Drill hole positions are labeled with black dots and black line indicates the boundary for the deposit based on >0.3% CuEQ grades.

Solids:

Table 1 provides drill-hole numbers and depth (see FIG. 7 for locations), X-ray diffraction identification, Cu isotope results, and Cu/Fe ratios. X-ray diffraction was used only when sufficient sample could be obtained, thus 6 samples do not have diffraction results. Sulfides such as pyrite, sphalerite, tetrahedrite and molybdenite were detected together with chalcopyrite in the mineral and rock powders.

TABLE 1

| Hole ID | Depth | Mineralization | Mineral | $d^{65}Cu$ | Cu/Fe |
|---|---|---|---|---|---|
| 4142 | 442 | Hypogene | Cpy, Pyr | 1.19 | 2.516 |
| 4142 | 707 | Hypogene | Cpy, Pyr | 0.78 | 2.782 |
| 4143 | 98 | Supergene | Cc, Pyr | −0.97 | 0.454 |
| 4182 | 860 | Hypogene | Pyr, cpy | 1.24 | 0.429 |
| 4202 | 206 | Supergene | Cc, Pyr | −0.25 | 0.856 |
| 4203 | 57 | Leach cap | Jar, Goe | −3.49 | 0.030 |
| 4203 | 82 | Leach cap | Jar, Goe | −1.27 | 0.039 |
| 4203 | 77 | Leach cap | Jar, Goe | −2.40 | 0.055 |
| 4203 | 200 | Supergene | Cc, Pyr | −0.51 | 1.099 |
| 4222 | 64 | Leach cap | Jar, Goe | −1.32 | 0.046 |
| 4222 | 182 | Supergene | Cc, Pyr | 1.27 | 0.122 |
| 4222 | 89 | Leach cap | Jar, Goe | −0.53 | 0.134 |
| 4222 | 129 | Supergene | Cpy, Pyr | 0.02 | 0.233 |
| 4223 | 88 | Leach cap | Jar, Goe | 0.68 | 0.010 |
| 4223 | 157 | Supergene | Pyr, Cov | −0.47 | 0.158 |
| 4223 | 133 | Supergene | Mal | −0.44 | 0.353 |
| 7360 | 3357 | Hypogene | Cc, Tetra | 0.14 | 0.980 |
| 7368 | 1925 | Hypogene | Cpy, Pyr | 0.62 | 0.039 |
| 7368 | 2023 | Hypogene | Q, Cpy, Pyr | −0.46 | 0.272 |
| 7368 | 2751 | Hypogene | Q, Cpy | −0.45 | 0.763 |
| 7368 | 2530 | Hypogene | Q, Cpy | −0.04 | 1.130 |
| 7374 | 1736 | Hypogene | Q, py, cpy | −0.39 | 0.249 |
| 7374 | 2268 | Hypogene | Q, | −0.25 | 0.366 |
| 7374 | 3341 | Hypogene | Q, Cpy | −0.19 | 0.899 |
| 7374 | 3614 | Hypogene | Q, Cpy | 0.02 | 1.076 |
| 7374 | 2075 | Hypogene | Pyr, Cc | 0.28 | 6.426 |
| 7377 | 2354 | Hypogene | Cpy, Pyr | −0.07 | 0.200 |
| 7377 | 2605 | Hypogene | Q, Pyr, Cpy | −0.19 | 0.283 |
| 7377 | 1939 | Hypogene | Q, Pyr, Cpy | 0.18 | 0.350 |
| 7377 | 3591 | Hypogene | Q, Cpy, Moly | −0.60 | 0.696 |
| 7377 | 2453 | Hypogene | Cpy | 0.11 | 0.831 |
| 7378 | 3326 | Hypogene | Q, Cpy | −0.20 | 0.138 |
| 7378 | 3053 | Hypogene | Q, Cpy | 0.12 | 0.793 |
| 7378 | 3917 | Hypogene | Q, Cpy | 0.02 | 0.798 |
| 7378 | 2561 | Hypogene | NA | 0.36 | 0.929 |
| 7378 | 2369 | Hypogene | Q, Cpy | 0.89 | 0.964 |
| 7379 | 2387 | Hypogene | Pyr, Tet | 0.82 | 5.542 |
| 7381 | 2073 | Hypogene | Cpy, Pyr | 0.54 | 0.491 |
| 7386 | 2552 | Hypogene | Spal, Pyr | 0.72 | 4.478 |
| 7389 | 2385 | Hypogene | Tetra | 0.22 | 5.134 |
| 8401 | 2580 | Hypogene | Q | −0.12 | 0.156 |
| 8401 | 1795 | Hypogene | Q, Cpy | 0.87 | 0.603 |
| 8401 | 3170 | Hypogene | Q, Cpy | −0.09 | 0.697 |
| 8401 | 2824 | Hypogene | Q, Cpy | −0.31 | 0.842 |
| 8401 | 1773 | Hypogene | Q, Cpy | 0.60 | 0.862 |
| 8401 | 1998 | Hypogene | Q, Cpy | −0.39 | 0.869 |
| 8413 | 2597 | Hypogene | Q, Cpy, Pyr | 0.11 | 0.743 |
| 8413 | 1747 | Hypogene | Q, Cpy | 0.45 | 0.879 |
| 8413 | 2869 | Hypogene | Q, Cpy | −1.48 | 0.909 |
| 8413 | 1998 | Hypogene | Q, Cpy | 1.39 | 1.037 |
| 8413 | 2226 | Hypogene | Q, Cpy | 0.07 | 1.131 |
| 8413 | 1629 | Hypogene | NA | 1.58 | 1.323 |
| 8417 | 2624 | Hypogene | Q, Pyr | −0.04 | 0.224 |
| 8417 | 3132 | Hypogene | Q, Ortho | 0.01 | 0.403 |
| 8417 | 1811 | Hypogene | NA | −0.12 | 0.486 |
| 8417 | 2934 | Hypogene | Q, Cpy | 0.36 | 0.945 |
| 8422 | 2919 | Hypogene | Cpy, Pyr | 1.11 | 0.553 |
| 8442 | 1075 | Hypogene | Q, Pyr | 0.63 | 0.004 |
| 8442 | 3074 | Hypogene | Pyr, cpy | −0.05 | 0.192 |

TABLE 1-continued

| Hole ID | Depth | Mineralization | Mineral | $d^{65}Cu$ | Cu/Fe |
|---|---|---|---|---|---|
| 8442 | 2324 | Hypogene | Q, Cpy | −0.60 | 0.653 |
| 8444 | 748 | Hypogene | Pyr | 0.29 | 0.003 |
| 8444 | 2550 | Hypogene | Q, Pyr | −0.94 | 0.003 |
| 8444 | 1498 | Hypogene | Q, Musc | 0.08 | 0.012 |
| 11527 | 1661 | Hypogene | NA | −0.46 | 0.133 |
| 11527 | 683 | Hypogene | Q, Ortho | −0.27 | 0.165 |
| 11529 | 1347 | Hypogene | Q, Ortho | −0.31 | 0.006 |
| 11529 | 2820.4 | Hypogene | Q, Musc | −0.24 | 0.016 |
| 11529 | 688.8 | Hypogene | Cpy, Pyr | 0.09 | 0.295 |
| 7391M | 476 | Hypogene | Cpy, Pyr | 2.11 | 0.321 |
| 7398M | 693 | Hypogene | Q, Ortho | −0.59 | 0.056 |
| 7398M | 494 | Hypogene | NA | −0.28 | 0.063 |
| 7398M | 893 | Hypogene | Q, Anorth | 0.59 | 0.070 |
| 7398M | 1170 | Hypogene | Q, Anorth | −0.03 | 0.088 |
| 7398M | 793 | Hypogene | Q, Cpy, Pyr | −0.18 | 0.169 |
| 8424M | 100 | Supergene | Cc, Pyr | −5.04 | 1.106 |
| 8425M | 39 | Supergene | Pyr, Cc | 1.88 | 0.042 |
| 8431M | 675 | Hypogene | Cpy, Pyr | 2.28 | 2.809 |
| 8440M | 1080 | Hypogene | Q, cpy, py | −0.08 | 0.169 |
| 8440M | 1657 | Hypogene | NA | −0.32 | 0.207 |
| 8440M | 786 | Hypogene | Q, cpy, pyr | −0.01 | 0.241 |
| 8440M | 832 | Hypogene | Q, Tetra | 0.57 | 0.447 |

The overall $\delta^{65}Cu$ isotopic range measured for the solid samples is between −5.0 and 2.2‰. The samples of supergene material display the largest range between −5.0 to 1.8‰, whereas the hypogene sulfide minerals range from −0.94 to 2.28‰. The average hypogene $\delta^{65}Cu$ is 0.18±0.65‰ (1σ, n=66). The cluster of hypogene values agrees with previous studies of Cu isotope fractionation at higher temperature (Ikehata et al., 2011; Li et al., 2009; Li et al., 2010; Maher and Larson, 2007; Mathur et al., 2009; Zhu et al., 2000). In contrast the average supergene samples display greater variation with average Fe-oxide (jarosite and goethite) $\delta^{65}Cu$ of −1.80±1.15‰ (1σ, n=5) and copper-rich supergene enrichment samples in $\delta^{65}Cu$ of −0.51±2.06‰ (1σ, n=9). The supergene Fe-oxides possess isotopically depleted values compared to the hypogene mineralization, which has been previously documented in studies of other deposits (Haest et al., 2009; Mathur et al., 2010; Mathur et al., 2009; Mirnejad et al., 2010).

Figure 8:
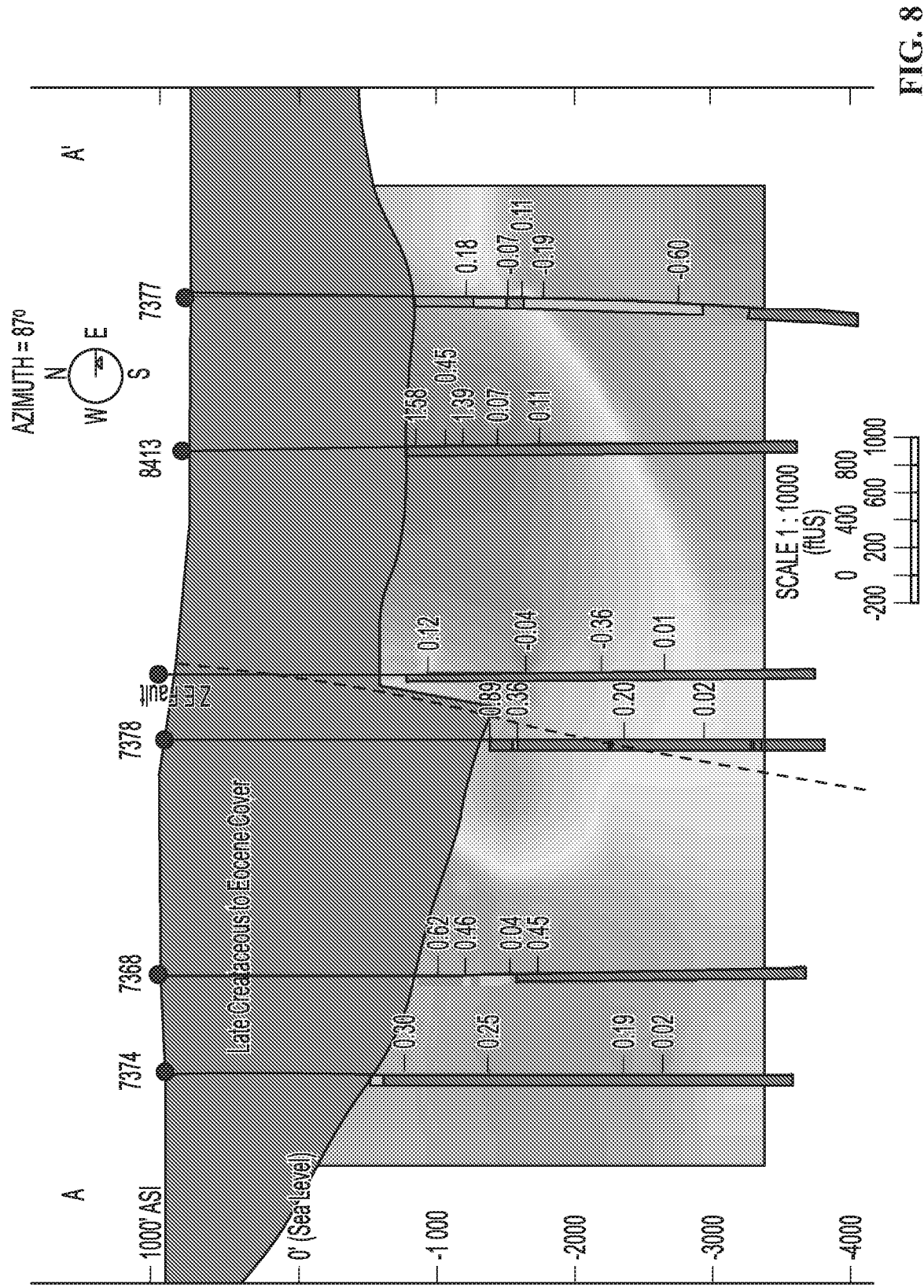
FIG. 8 shows the cross section A-A' (see FIG. 7) trending northeast-southwest across the eastern part of the Pebble deposit showing Cu isotope ratios. The dashed line indicates the location of a fault. The scale is 1:10000. The bar at the surface is indicated to be 1000 feet above see level, each marker represents a 1000 foot drop in depth, thus, the second marker is at sea level and the third marker is 1000 feet below sea level, as such the bottom marker is 4000 feet below sea level. The horizontal bar starts at −200 (far left) and goes to 1000 (far right).
Figure 9A:
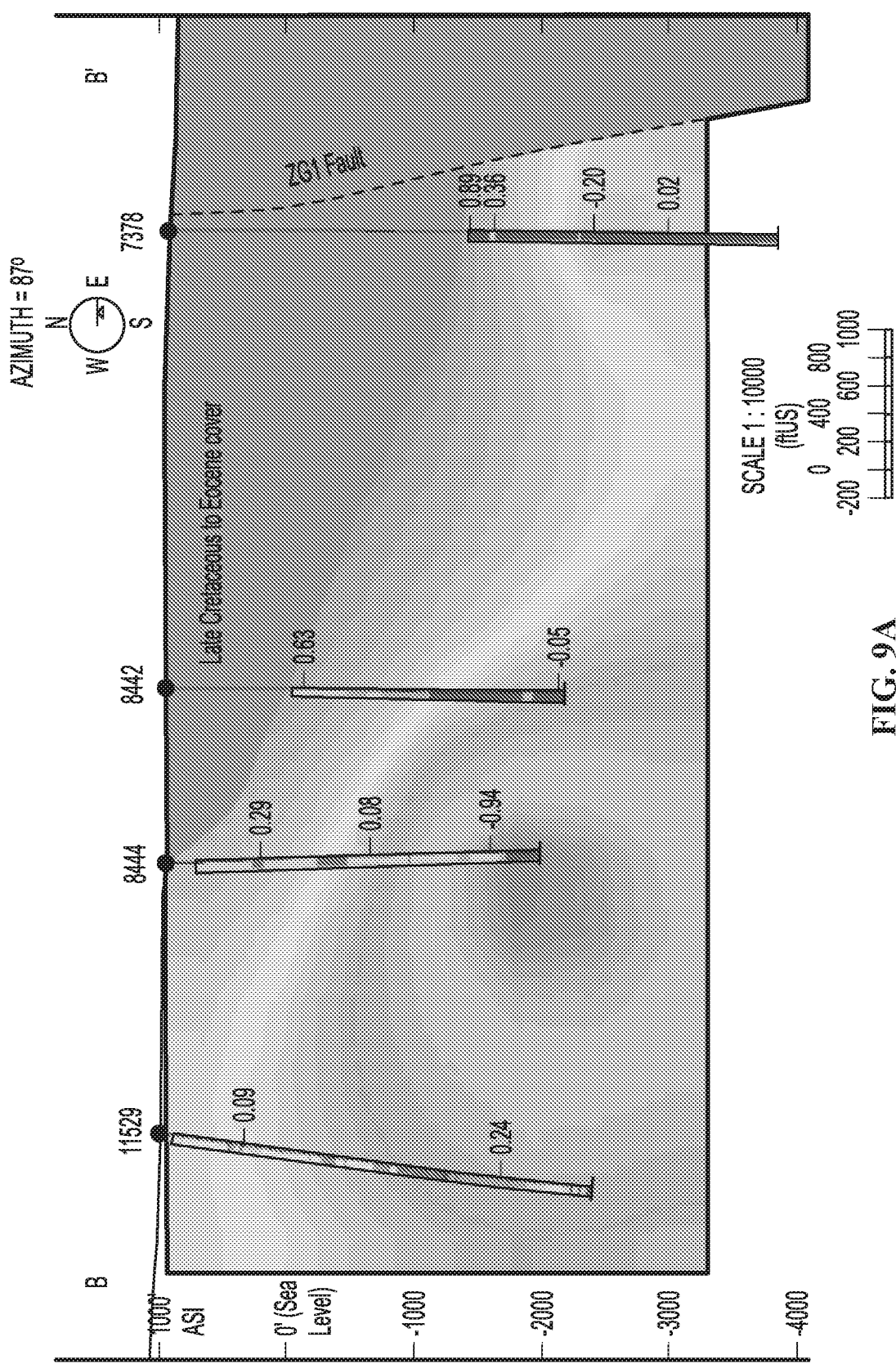
FIG. 9A) shows A) Cross section B-B' (see FIG. 7) trending east-west across the southern part of the Pebble deposit showing Cu isotope ratios. B) shows the Cu isotope compositions superimposed on alteration zones (from Gregory et al.) and the E-W cross section of the Pebble deposit with Cu isotope ratios.
Figure 9B:
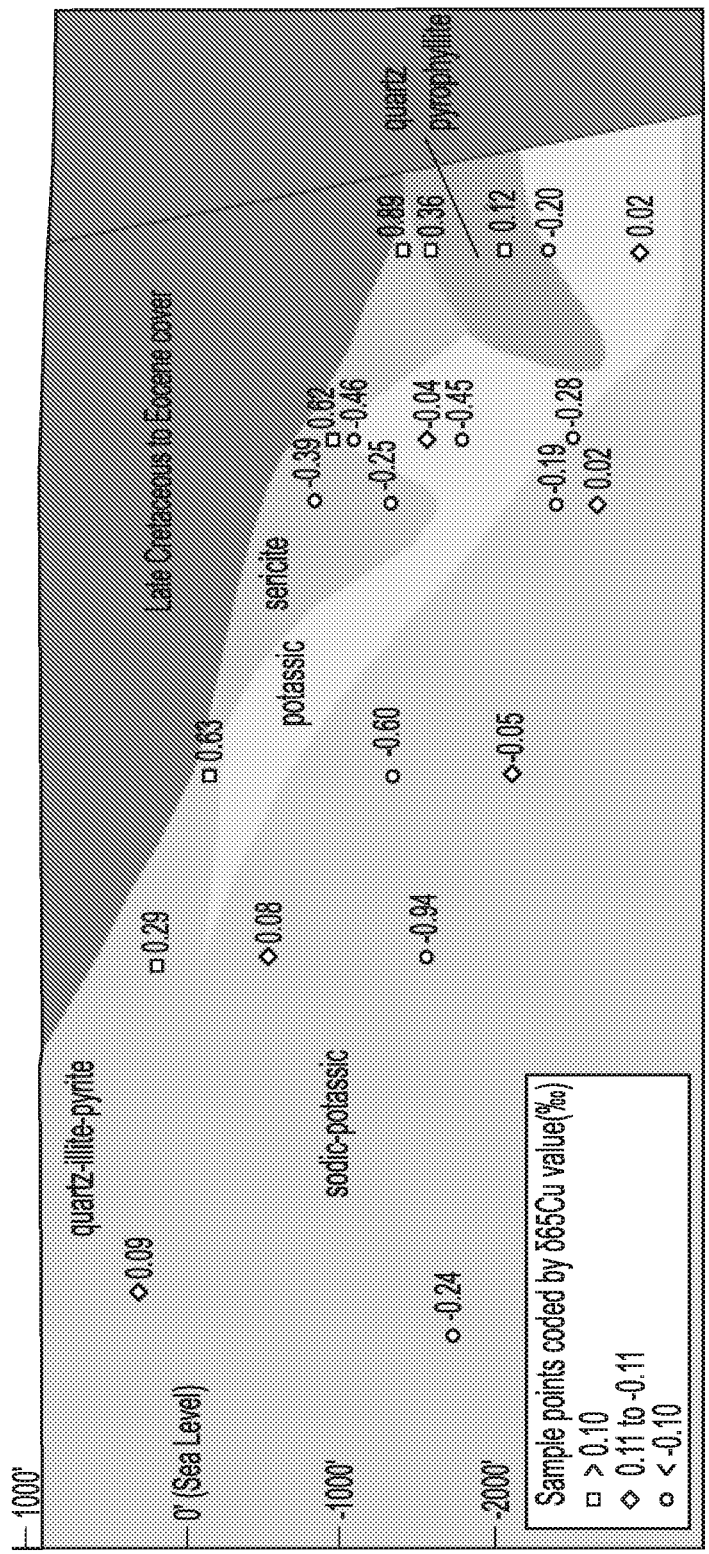
FIG. 9B shows the Cu isotope composition and silicate alteration on the same E-W cross section. The bar at the surface is indicated to be 1000 feet above sea level, each marker represents a 1000 foot drop in depth, thus, the second marker is at sea level and the third marker is 1000 feet below sea level.

Copper isotope compositions of hypogene samples were contoured using the Geosoft Oasis Montaj computer program. Samples from drill cores that lie near the North-South or East-West cross section line on FIG. 7 were chosen for contouring. Samples with clear supergene mineral assemblages such as Fe-oxides, chalcocite or copper oxides are not considered for contouring. A total of nine drill holes are included in Cu isotope contouring because their spatial location allows for projection onto NE-SW and E-W cross sections. A total of 26 values are contoured for the NE-SW section and 12 values for the E-W section. Four values were not included in the contoured data as the values were too high for the range selected by the contouring program. Patterns of the Cu isotope ratios vary with depth, basic mineralogy, and the type of silicate alteration present. FIGS. 8 and 9 are cross sections taken from NE-SW and E-W in the deposit. The contoured Cu isotope values show a pattern where lighter (depleted) values characterize deeper samples and higher temperature silicate alteration assemblages in both cross sections. The pattern of increasing isotopic ratios from depth to shallow levels appears to be offset along the ZE fault (FIG. 8)

Figure 10:
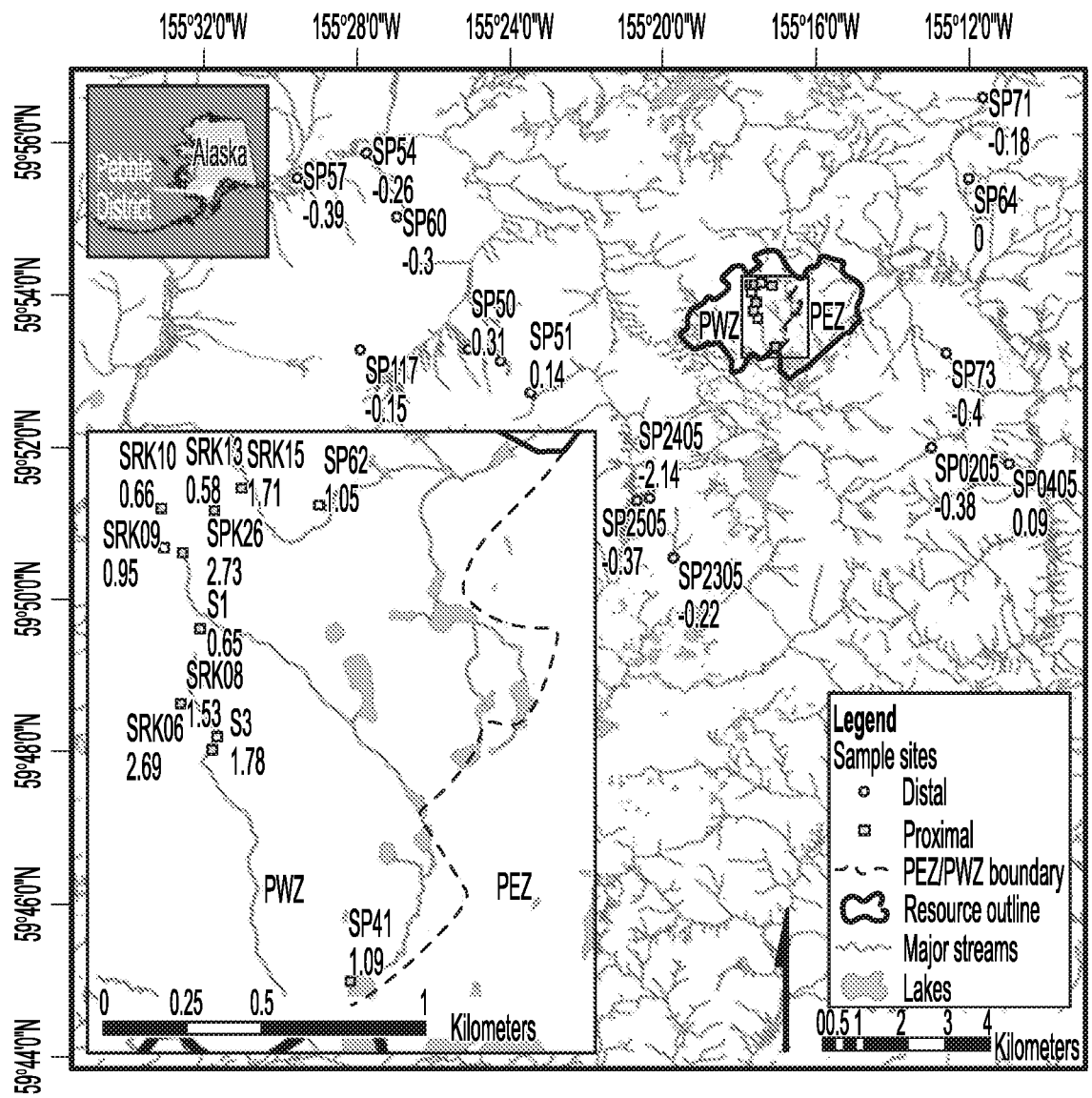
FIG. 10 is a map showing Cu isotope ratios in seep waters both proximal and distal to the deposit.
Figure 11:
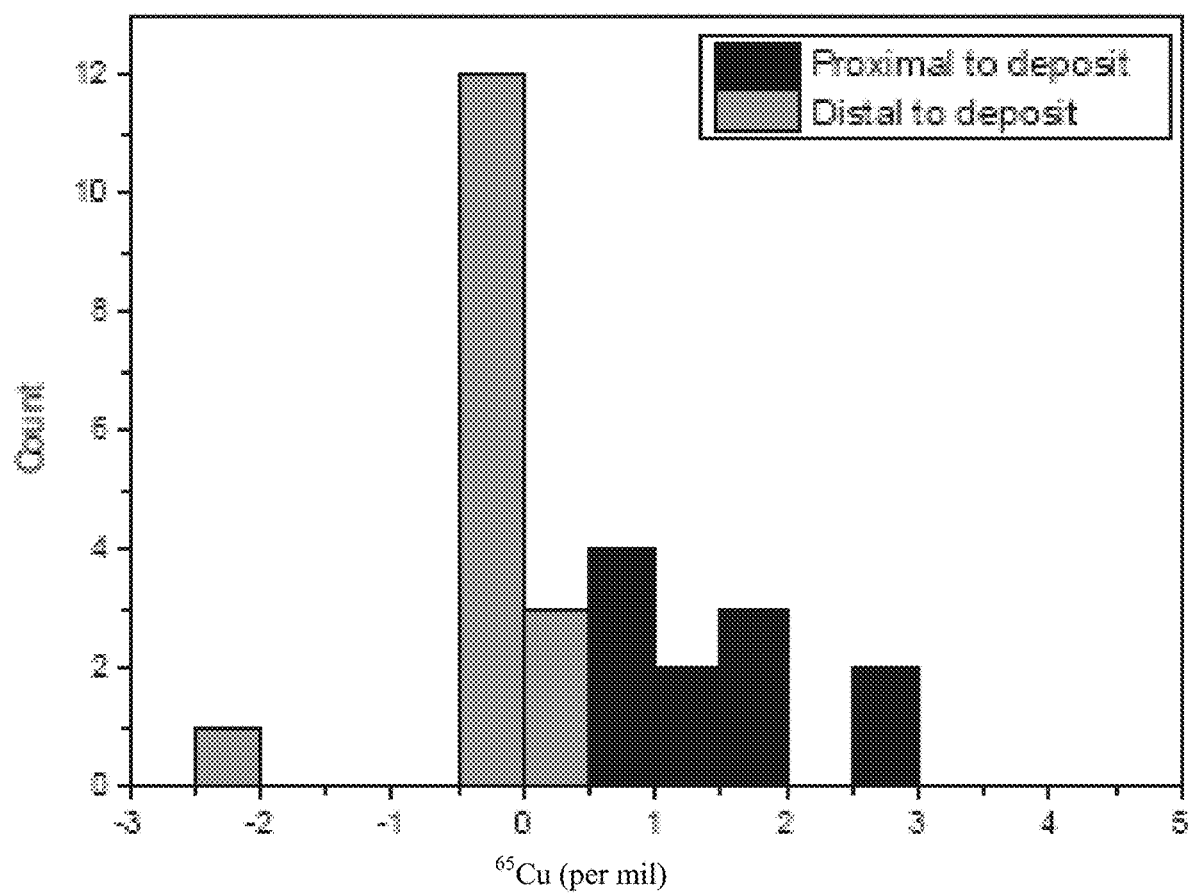
FIG. 11 shows the frequency diagram of Cu isotope values of the seeps from 2011.

Waters:

The copper isotopic compositions of stream and seep waters range from −0.40 to 4.12‰. The water values span those reported by other investigators (Borrok et al., 2008; Kimball et al., 2009; Vance et al., 2008). The seep water compositions vary depending on their proximity to the deposit. FIGS. 10 and 11 show that seep waters have high $\delta^{65}Cu$ signatures proximal to the deposit and lower $\delta^{65}Cu$ signatures distal to the deposit.

Figure 12:
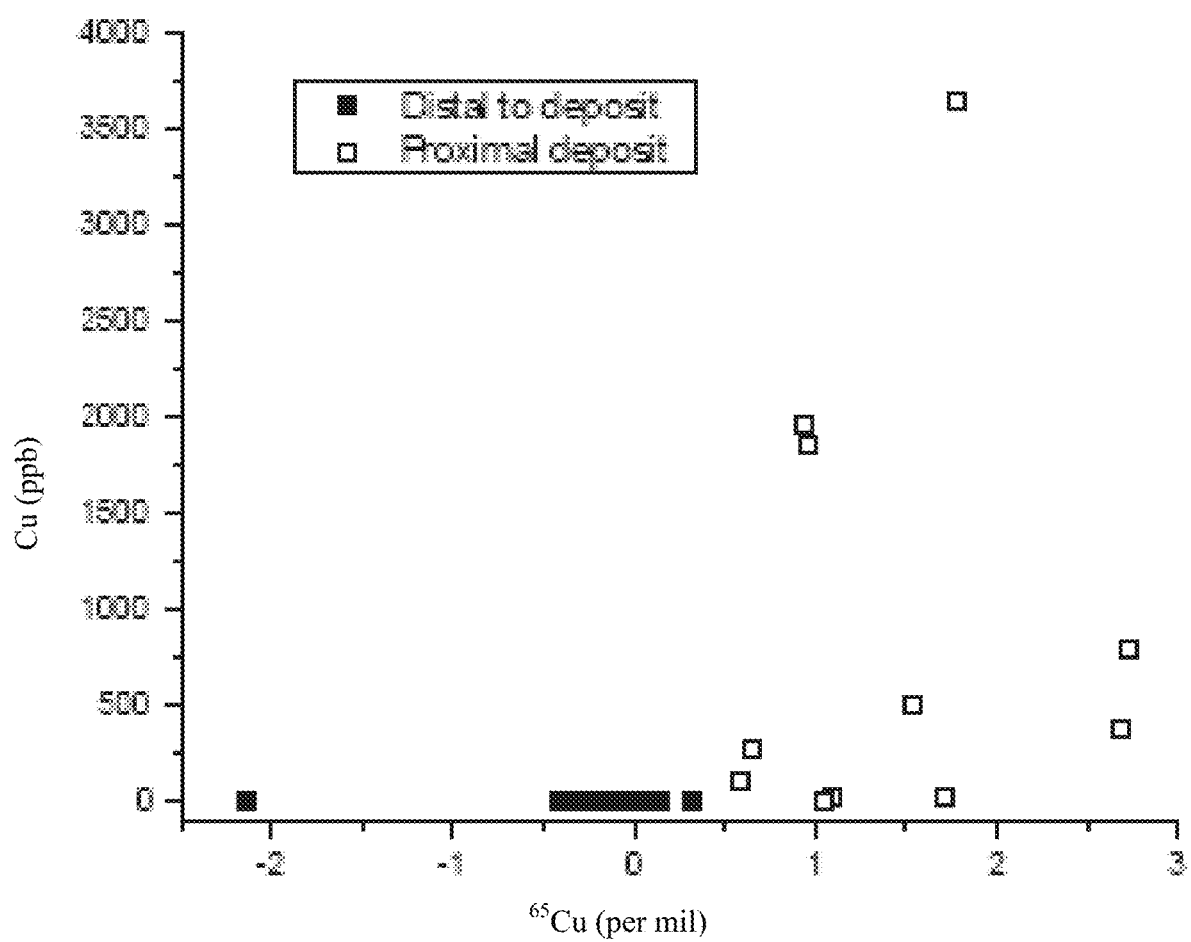
FIG. 12 shows the Cu isotope versus Cu concentrations (in ppb) for 2011 seep data.

Copper concentrations in the seep samples range from 0.3 to 3,700 ppb, which incorporates the range reported by (Eppinger, This volume). FIG. 12 indicates that the highest concentrations of Cu correlate with the highest $\delta^{65}Cu$ isotope values measured in the waters. Interestingly, many seep samples with low Cu concentrations (approximately 10 ppb) possess $\delta^{65}Cu$ ratios that are much greater (>2 per mil) than stream and river average values (0.77±0.4‰ (n=59) reported by Vance et al., (2008).

Waters were analyzed that were collected from the same location and the same month (mid-late August) in 2009 and 2010 to test the long term change in the $\delta^{65}Cu$ signals of the waters (FIG. 5). A line with a slope of 1 is plotted and the $r^2$ value of this line is 0.91. Thus, samples taken from the same time of year have a similar isotopic composition. In contrast, samples from 2011 were taken in early July. The 2011 samples have slightly lower $\delta^{65}Cu$ isotope values compared to those collected in 2009 and 2010, indicating that there could be some seasonal affect to the measured $\delta^{65}Cu$. The potential seasonal variation, however, does not significantly impact differentiation between waters proximal and distal to the deposit.

The Fe-oxides collected from the seep bed have variable concentrations of Cu from 0.5 to 0.9 ppm. The $\delta^{65}Cu$ in the Fe-oxides are lower than the water derived from the seep (Table 2).

TABLE 2

| | | 2009 | | 2010 | | 2011 | |
|---|---|---|---|---|---|---|---|
| Sample | Type | $d^{65}Cu$ (per mil) | Cu (ppb) | $d^{65}Cu$ (per mil) | Cu (ppb) | $d^{65}Cu$ (per mil) | Cu (ppb) |
| S26 | seep | 3.57 | 720.1 | 2.49 | n.a. | 2.73 | 790.0 |
| S01 | seep | 3.22 | 507.2 | 3.23 | n.a. | 0.65 | 1854.0 |
| S03 | seep | 4.21 | 2282.9 | 3.04 | n.a. | 1.78 | 3652.0 |
| S04 | stream | 1.04 | 6.9 | 0.98 | n.a. | n.a. | n.a. |
| SK100G | stream | 1.19 | 2.6 | −0.08 | n.a. | n.a. | n.a. |
| SK100D | stream | −0.08 | 1.1 | 0.07 | n.a. | n.a. | n.a. |
| SRK11 | seep | 1.92 | 66.6 | 2.08 | n.a. | n.a. | n.a. |
| SRK15 | seep | 2.66 | 10.8 | 3.19 | n.a. | n.a. | n.a. |
| UT146A | stream | 0.67 | 0.3 | n.a. | n.a. | n.a. | n.a. |
| SRK 12 | seep | n.a. | n.a. | 4.12 | n.a. | n.a. | n.a. |

TABLE 2-continued

| Sample | Type | 2009 d$^{65}$Cu (per mil) | 2009 Cu (ppb) | 2010 d$^{65}$Cu (per mil) | 2010 Cu (ppb) | 2011 d$^{65}$Cu (per mil) | 2011 Cu (ppb) |
|---|---|---|---|---|---|---|---|
| SRK 13 | seep | n.a. | n.a. | 1.66 | n.a. | n.a. | n.a. |
| SRK01 | seep | n.a. | n.a. | 0.70 | n.a. | n.a. | n.a. |
| SK124A | seep | n.a. | n.a. | −0.59 | n.a. | n.a. | n.a. |
| S44 | seep | n.a. | n.a. | 0.54 | n.a. | n.a. | n.a. |
| SK 100C | seep | n.a. | n.a. | −0.08 | n.a. | n.a. | n.a. |
| SP0205D | seep | n.a. | n.a. | n.a. | n.a. | −0.38 | 1.2 |
| SP0405 | seep | n.a. | n.a. | n.a. | n.a. | 0.09 | 0.3 |
| SP117 | seep | n.a. | n.a. | n.a. | n.a. | −0.15 | b.d. |
| SP2305 | seep | n.a. | n.a. | n.a. | n.a. | −0.22 | 0.6 |
| SP2405 | seep | n.a. | n.a. | n.a. | n.a. | −2.14 | 0.8 |
| SP2505 | seep | n.a. | n.a. | n.a. | n.a. | −0.37 | 0.5 |
| SP30 | seep | n.a. | n.a. | n.a. | n.a. | −0.06 | b.d. |
| SP41 | seep | n.a. | n.a. | n.a. | n.a. | 1.09 | 18.8 |
| SP50 | seep | n.a. | n.a. | n.a. | n.a. | 0.31 | b.d. |
| SP51 | seep | n.a. | n.a. | n.a. | n.a. | 0.14 | b.d. |
| SP54 | seep | n.a. | n.a. | n.a. | n.a. | −0.26 | 0.5 |
| SP54D | seep | n.a. | n.a. | n.a. | n.a. | −0.07 | 0.5 |
| SP57 | seep | n.a. | n.a. | n.a. | n.a. | −0.39 | 0.5 |
| SP60 | seep | n.a. | n.a. | n.a. | n.a. | −0.30 | 1.7 |
| SP62 | seep | n.a. | n.a. | n.a. | n.a. | 1.05 | 0.3 |
| SP64 | seep | n.a. | n.a. | n.a. | n.a. | 0.00 | b.d. |
| SP71 | seep | n.a. | n.a. | n.a. | n.a. | −0.18 | b.d. |
| SP73 | seep | n.a. | n.a. | n.a. | n.a. | −0.40 | b.d. |
| SRK06 | seep | n.a. | n.a. | n.a. | n.a. | 2.69 | 373.0 |
| SRK08 | seep | n.a. | n.a. | n.a. | n.a. | 1.53 | 494.0 |
| SRK09 | seep | n.a. | n.a. | n.a. | n.a. | 0.95 | 1962.0 |
| SRK10 | seep | n.a. | n.a. | n.a. | n.a. | 0.66 | 269.0 |
| SRK13 | seep | n.a. | n.a. | n.a. | n.a. | 0.58 | 110.8 |
| SRK15 | seep | n.a. | n.a. | n.a. | n.a. | 1.71 | 16.1 |
| S-3 | Fe-oxide | 1.92 | 900.00 | n.a. | n.a. | n.a. | n.a. |
| SP-26 | Fe-oxide | 0.43 | 544.00 | n.a. | n.a. | n.a. | n.a. |
| SRK-15 | Fe-oxide | 0.98 | 652.00 | n.a. | n.a. | n.a. | n.a. |

Figure 13:
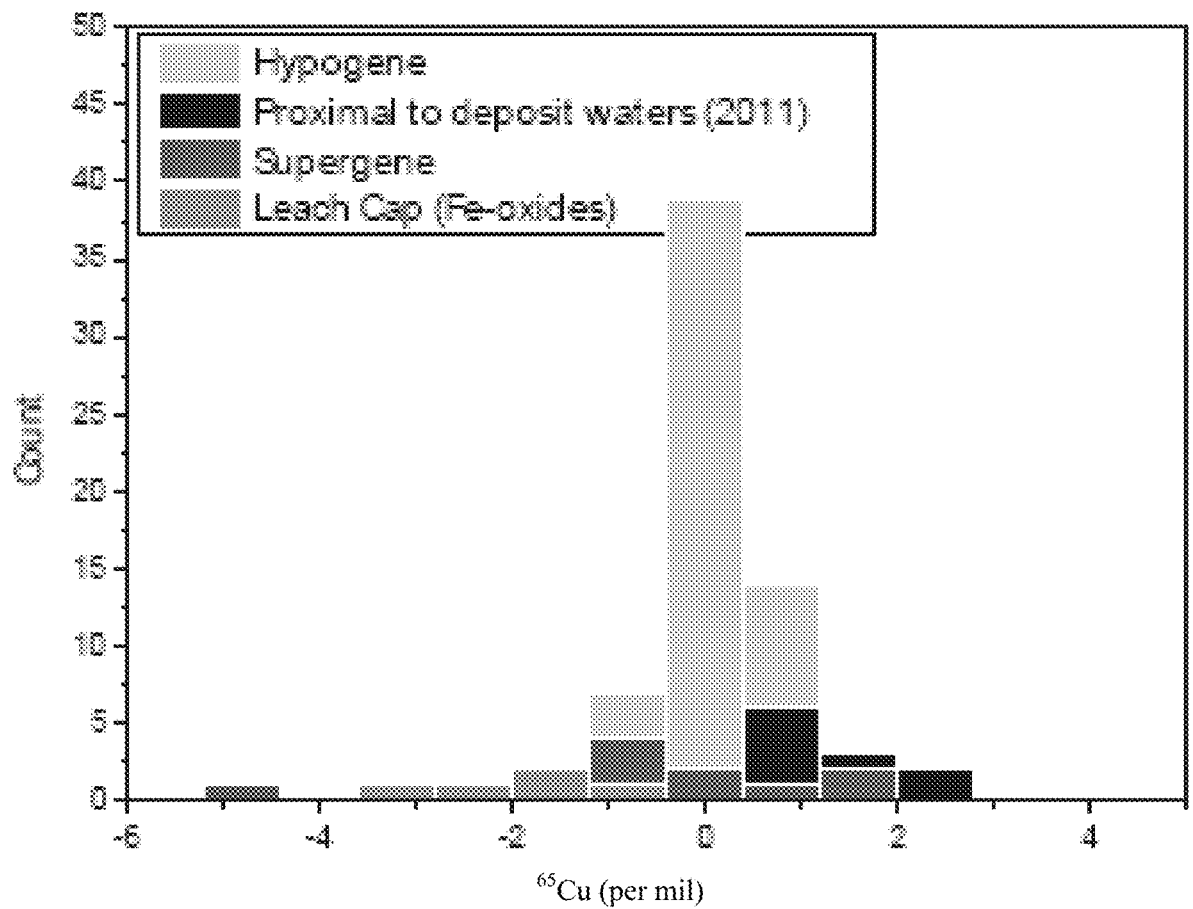
FIG. 13 shows the Cu isotope compositions of all samples collected from the Pebble deposit area where leach cap samples are Fe-oxides and supergene are Cu-rich sulfides.

Relationship Between Solids and Waters:

FIG. 13 illustrates the isotopic variation of the hypogene samples, weathered products (from the leach cap and underlying supergene zone), seep and stream waters proximal to the deposit. Proximal waters have relatively high $\delta^{65}$Cu isotope values compared to leached weathered products. The supergene copper minerals have a range of $\delta^{65}$Cu values, but most are isotopically heavy and overlap with hypogene rocks and minerals. The overall distribution of the samples illustrates that oxidizing waters have the highest compositions, the bulk of the hypogene and supergene rocks overlap and center around zero per mil, and the Fe-oxide leach cap minerals have the lightest values have the lowest values Discussion:

The Cu isotope data presented here reveal information about both the ancient high-temperature hydrothermal system at Pebble and the active hydrogeologic system. This discussion first focuses on the development of the hypogene high-temperature hydrothermal system through spatial analysis of the Cu isotope fractionation and associated silicate mineralogy. The second part of the discussion explains how weathering of the minerals formed at high-temperature can be used to fingerprint buried or concealed deposits. Both aspects have significant implications and potential applications for exploration.

High-Temperature Hydrothermal System:

The fractionation of Cu isotopes at high-temperatures has received little attention. To date, two experimental studies (Maher et al., 2011; Seo et al., 2007) and three field studies (Li et al., 2009; Li et al., 2010; Maher and Larson, 2007) have demonstrated that there is predictable and measurable copper isotopic variation in nature. The studies pointed out that fractionated Cu isotope values of sulfides collected at the surface could indicate ores at depth. None of the datasets have clearly identified contoured spatial patterns in the Cu isotope ratios from porphyry copper deposits. The current study includes samples across the entirety of the known Pebble deposit and therefore, assessment of the vertical and lateral zoning in copper isotope signatures and the link to the environmental signature of this Cu porphyry deposit are possible. Both of these are novel contributions to this field of study.

The cross sections in FIGS. 8 and 9 show spatial patterns of the copper isotope compositions. Isotopically heavier and lighter samples occur in the shallower and deeper parts of the deposit, respectively. No specific range of copper isotope values correlates with alteration type. For example, the potassic alteration does not possess a defined small range in copper isotopic composition but rather, covers the range of all hypogene measured values (FIG. 8 potassic alteration $\delta^{65}$Cu ranges from −1.49 to +1.58). However, the patterns of alteration and Cu isotope contours mimic each other in the E-W cross section (FIG. 9). Maher and Larson (2007) described a similar pattern of isotopically light values near core skarn mineralization and isotopically heavy values in the outer portions of the deposit.

The possible causes for the measured Cu isotope variation are multiple, complex and cannot simply be explained with the empirical relationships displayed here. Redox changes, pH, temperature, and other factors (Maher and Larson, 2007; Seo et al., 2007) have been presented as explanations for the measurable Cu isotopic fractionation in sulfides associated with higher temperature silicate alteration minerals. Much more applied and empirical work is required to document all possible pathways for fractionation that could be associated with the transport of Cu by vapor, brine or supercritical fluids, and precipitation during hydrothermal activity. Seo et al. (2007) provided theoretical calculations based on equilibrium isotope fractionation, which clearly demonstrated predictable Cu isotope fractionation with cooling and precipitation of Cu.

The similarity between Cu isotope composition and alteration type (FIG. 9B) indicates that temperature and pH may be an important factor in the fractionation of Cu isotopes. The positive values in the data are confined to the quartz-illite-pyrite, sericite and quartz-pyrophyllite alteration zones. Negative values are confined to the potassic and sodic-potassic domains. The quartz-illite-pyrite, sericite, and quartz-pyrophyllite alteration types are the result of 300-400° C. acidic alteration (Gregory et al., this volume) that followed the initial higher temperature and possibly more neutral alteration event that produced potassic and sodic-potassic alteration. Li et al. (2010) presented temperature-based fractionation factors ($\Delta_{sol-sulfide}$ of −0.2 to 0.4) for a theoretical solution with a starting $\delta^{65}Cu$ ratio of 0.2‰. Utilizing this method, and assuming a fractionation factor of 0.4, the range of Cu isotope values of precipitated Cu minerals can be explained and predicted. The first precipitated copper minerals closest to the source would be depleted in $^{65}Cu$ and as the more copper is precipitated from the solution the copper minerals would become more enriched in the $^{65}Cu$ isotope.

The predicted isotopic composition of copper minerals using this fractionation factor matches the isotopically light core and heavy outer portions of the Pebble deposit. To date, no published data exist for the fluids at Pebble, however the general paragenetic sequence indicates that initial precipitation of Cu as sulfides took place during potassic and sodic-potassic alteration at depth, followed by precipitation in shallower portions of the system (Lang et al., This volume). The Cu isotope data supports this observation. Early hotter fluids in deep parts of the deposit deposited Cu minerals with low isotopic compositions, followed by deposition of Cu minerals in shallow portions by later lower temperature fluids which produced higher $\delta^{65}Cu$ values. The lower temperature second alteration event (quartz-pyrophyllite and sericite zones) overprinted earlier alteration and mineralization and it is possible that the lower temperature overprint caused the most fractionated values in the eastern portion of the deposit. This may be evidenced by the fact that all $^{65}Cu$ values in samples from core through the eastern part of the deposit are low (FIG. 8). The sericitic and quartz-pyrophyllite alteration events have been interpreted (Lang et al. this volume) to have formed by lateral flow of fluids in the upper parts of the system, and could explain this trend. Equally interesting is how a post-mineralization fault displaces the isotopic pattern (FIG. 8), suggesting that the isotopic compositions reflect fluid pathways that were pre-faulting.

A thin, incompletely developed zone of supergene mineralization occurs in the Pebble West Zone, overlain by a thin leached cap (Lang et al., this volume). We collected thirteen samples from the supergene zone (Table 1), six of which are considered leach cap samples (those with jarosite and goethite). The leach cap (samples with Fe-oxides in Table 1) samples have low $\delta^{65}Cu$ isotope signatures compared to the hypogene rocks (FIG. 13). This has been documented in several previous studies (Haest et al., 2009; Mathur et al., 2010; Mathur et al., 2009; Mirnejad et al., 2010) and most likely indicates a preference for the $^{65}Cu$ isotope in solution during weathering, resulting in isotopically light residual Fe-oxide compositions (the process is more fully described in later sections). The use of leach cap Cu isotope values in arid climates provides important information for the exploration geologist (Mathur et al., 2010; Mirnejad et al., 2010). Supergene chalcocites and Cu-oxides samples have been shown to possess the enriched $^{65}Cu$ signature derived from the oxidative weathering of minerals in the leach cap. In other words, the oxidative weathering of hypogene sulfides results in producing Fe-oxide leach cap minerals that possess Cu isotope compositions that are depleted in $^{65}Cu$. The oxidative solutions that transport and provide copper for chalcocite in the supergene enrichment minerals possess Cu isotope compositions that are enriched in $^{65}Cu$. The Cu isotope values span the range of all solids measured at Pebble and most likely indicate supergene mineralization is currently being weathered.

Low Temperature Hydrogeologic System:

The Cu isotope composition of stream and seep water samples aid our understanding of the current weathering processes Several studies have clearly identified that the oxidizing leaching of Cu-rich sulfide minerals leads to the preferential release of the $^{65}Cu$ isotope into solution with a fractionation of about 3‰ (Balistrieri et al., 2008; Borrok et al., 2008; Kimball et al., 2009; Wall et al., 2011a). Different minerals produce slightly different $\Delta_{liquid-solid}$ fractionation factors but most are above 1‰. Wall et al. 2011 and Mathur and Schlitt (2010) summarize how the fractionation factors for sulfide minerals can be applied to natural systems. The fractionation factors suggest that waters actively weathering sulfides should possess enriched $\delta^{65}Cu$ signatures compared to average stream surface waters of approximately 0.9‰ (Archer, 2004; Bermin et al., 2006; Vance et al., 2008). The $\delta^{65}Cu$ values in water proximal to the deposit are as high as 4.2‰.

Seep waters represent shallow groundwater that interacted with the till and the bedrock. We interpret seep waters to indicate weathering of till and bedrock near (<100 m) the source of the seep but the seeps could represent some water component from depths greater than 100 m. The most extensive sampling of seeps occurred in 2011; therefore, only the 2011 seep sample locations and Cu isotope values are shown in FIG. 10. As seen on FIG. 10, waters located proximal to the deposit (average $\delta^{65}Cu$=1.4‰±0.7 1σ) have an isotopic signature that is distinctly higher in comparison to distal areas (average $\delta^{65}Cu$=−0.27‰±0.5 1σ; FIG. 10A). These patterns suggest that oxidation of Cu-rich sulfides in the deposit results in enriched $\delta^{65}Cu$ compositions in proximal seeps compared to distal seeps. The relatively scant data from oxidative weathering of non-Cu-rich sulfide minerals (Balistrieri et al., 2008; Bigalke et al., 2010; Bigalke et al., 2009; Bigalke et al., 2011; Pokrovsky et al., 2008; Zhu et al., 2002) reveals that fractionation factors are <1‰ and therefore, the isotopically heavy signatures present at Pebble were mostly likely derived by weathering of Cu-rich sulfides However, the seeps distal from the deposits with values near 0 per mil indicate the absence of significant weathering of Cu-sulfide minerals or weathering of non-Cu-rich minerals. Comparison of seep waters both proximal and distal to the deposit shows very little overlap (FIG. 10) Clearly the seep data identify where the location of the concealed Pebble deposit.

Other possible hypothesis could be used to explain the relative differences in isotopic composition between distal and proximal samples and these could be documented with further study. However, the data indicate that the technique is successful in identifying concealed deposits.

The relationship between the Cu isotope composition and Cu concentration in seep waters (FIG. 12) suggests an important advantage of the former in delineating concealed mineralization. Specifically, multiple samples proximal to the deposit have less than 50 µg/L dissolved Cu (relatively low Cu concentration), yet have high Cu isotope compositions indicative of mineralization (FIG. 12). Thus, Cu concentration data alone may target sulfide mineralization. However, the enriched $\delta^{65}Cu$ isotope signatures of these water samples with relatively low Cu concentrations indicate Cu-rich sulfides as the source. Important for exploration, yearly effects have an insignificant impact on the use of this exploration tool. In 2009 and 2010, we sampled the same sites during mid to late August) (FIG. 5). A good correlation exists between the 2009 and 2010 data.

In contrast, the 2011 data were collected in early July and all samples from similar sites possess significantly lighter values. This indicates that seasonal effects may impact the Cu isotope signature. The cause for the variations seen between samples collected in July versus August could be related to kinetics. Wall et al. (2011) demonstrate the impact of kinetics on the oxidative weathering of Cu sulfide. They discovered that increased concentrations of ferric sulfate in the solution accelerate the dissolution of copper from bornite and result in isotopically light solutions compared to leach solutions with less ferric sulfate. The data revealed the impact of kinetics on the overall process of leaching bornite and the importance of the role of redox changes in the mineral during dissolution. The Pebble data could be reflecting a similar process. Regardless, the copper isotope variation between the seep waters proximal and distal to the deposit exists during single sampling campaigns and reveals the covered deposit.

Geologic exploration in areas with similar climate and with identified potential concealed targets identified by geophysics should include, seep water sampling because of the demonstrated signature of active weathering of Cu-rich sulfide minerals. Pond water may also be useful because Eppinger et al. (this volume) show that many ponds in the vicinity of mineralization have high Cu concentrations. However, the copper isotope compositions have not yet been analyzed.

Figure 6:
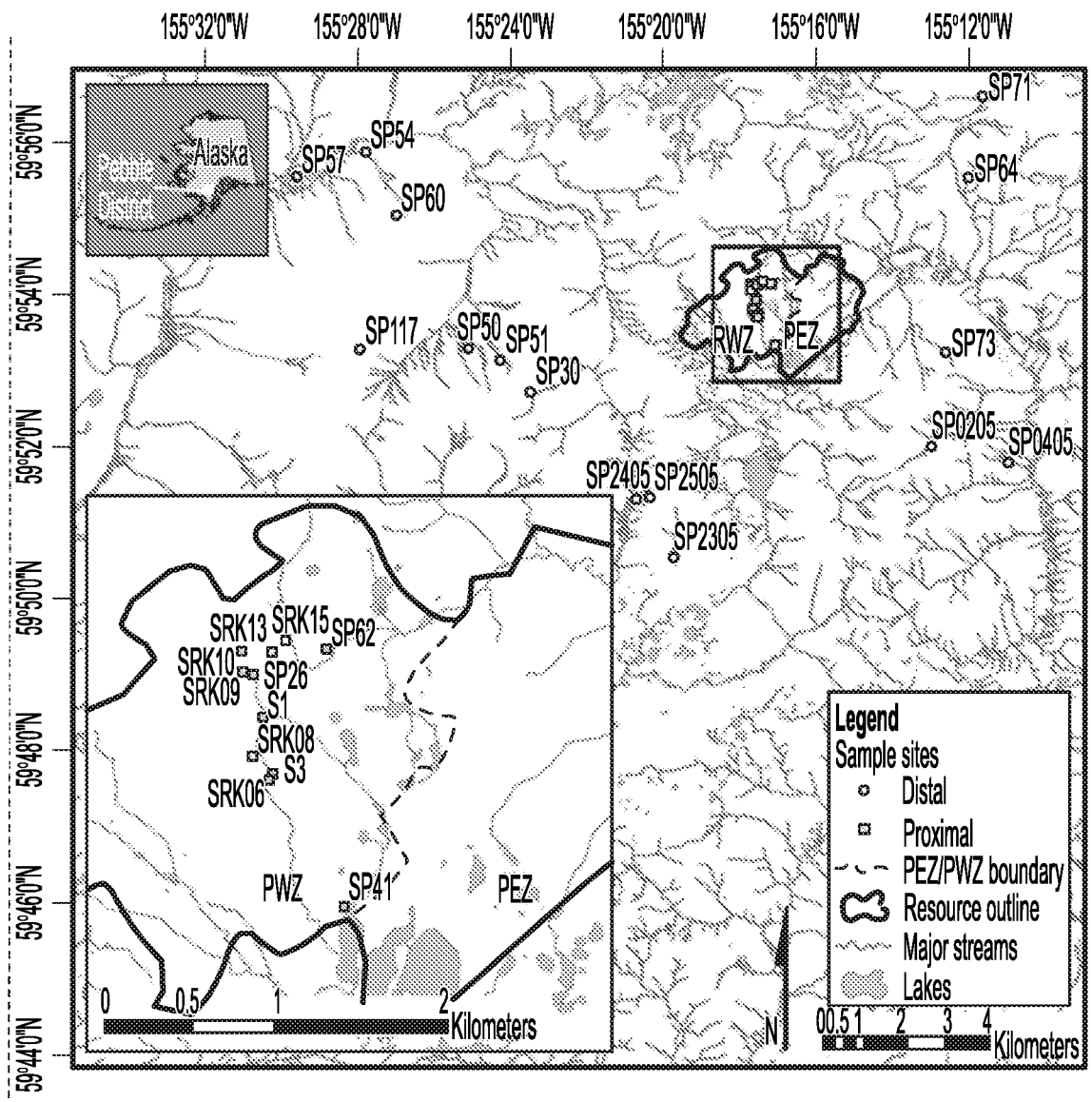
FIG. 6 shows the Location map of the Pebble deposit showing the seep and stream water sample locations. Sample locations are indicated by dots, and the outline of the deposit is in the circle.

The density of sampling is an important aspect of exploration, as it obviously depends on the technique used. The results presented here show that the deposit is targeted with 50-60 samples over a relatively large geographic area (FIG. 6, 10). In unknown areas, the density is determined in part by the distribution of seeps and ponds, but as this study shows, Cu isotope measurements, in addition to copper concentration data, are likely to provide information about the potential for have concealed deposits.

Conclusion:

The full potential of copper isotope fractionation in sulfide minerals to vector to the source is now being realized. Sample sets such as these (n~60) provide insight to fluid flow. Due to the general enrichment of the isotopic ratios from the source of mineralization characterized here and at other locations; the use of vectoring with high-temperature mineralization works. At lower temperature supergene processes discern paleo-fluid pathways.

With regards to surface fluids, the isotopic data provides exploration geologists with more information than concentration data alone. The data from Pebble show that high Cu isotope values characterize samples proximal to the deposit even though copper concentrations are low. Since seasonal affects may impact the dataset, sampling of waters should occur over a short time interval (two weeks).

(e) Example 4—Protocol for Analyzing Cu Isotopes

The following protocol can be used to determine the Cu concentration in a solution.

1. Dry appropriate volume of solution for Ion chromatography in a 60 ml savillex at 40 degrees C. overnight
2. Prep column—add 1.6 to 1.8 AGI MP1 200-400 resin let 8 ml MQ water, 8 ml 0.5N HNO3, 6 ml 6N HCl resins are ready for the sample
3. Add 2 ml of 6N HCl to dried sample cover sample with lid and warm on hot plate (40-60 degrees C.) for 10 minutes take solution of hot plate and cool
4. Add 2 ml of 6N HCl sample to the resin
5. Add 6 ml 6N HCl and drain
6. Collect next 28 ml of 6N HCl
7. Dry 28 ml of sample overnight on hot plate
8. Add 2 ml of 0.5N HNO3 to prep for instrument
9. Centrifuge 2 ml solutions for 2 minutes
10. Take 1.8 ml of the solution and filter with 150 micron filter (filters have been acid rinsed then MQ water before each filtration)

4. REFERENCES (a) References for Example 1

Asael, D., Matthews, A., Bar-Matthews, M., and Halicz, L., 2007, Copper isotope fractionation in sedimentary copper mineralization (Timna Valley, Israel): Chemical Geology, v. 243, p. 238-254.

Asael, D., Matthews, A., Oszczepalski, S., Bar-Matthews, M., and Halicz, L., 2009, Fluid speciation controls of low temperature copper isotope fractionation applied to the Kupferschiefer and Timna ore deposits: Chemical Geology, v. 262, p. 147-158.

Haest, M., Muchez, P., Petit, J. C. J., and Vanhaecke, F., 2009, Cu isotope variations in the Dikulushi Cu—Ag deposit, DRC: Of Primary origin or induced by supergene reworking?: Economic Geology, v. 104, p. 1055-1064.

Kimball, B. E., Mathur, R., Dohnalkova, A. C., Wall, A. J., Runkel, R. L., and Brantley, S. L., 2009, Copper isotope fractionation in acid mine drainage: Geochimica et Cosmochimica Acta, v. 73, p. 1247-1263.

Larson, P. B., Maher, K., Ramos, F. C., Chang, Z., Gaspar, M., and Meinert, L. D., 2003, Copper isotope ratios in magmatic and hydrothermal ore-forming environments: Chemical Geology, v. 201, p. 337-350.

Maher, K. C., and Larson, P. B., 2007, Variation in Copper Isotope Ratios and Controls on Fractionation in Hypogene Skarn Mineralization at Coroccohuayco and Tintaya, Peru: Economic Geology, v. 102, p. 225-237.

Mathur, R., Ruiz, J., Titley, S., Liermann, L., Buss, H., and Brantley, S. L., 2005, Cu isotopic fractionation in the supergene environment with and without bacteria: Geochimica et Cosmochimica Acta, v. 69, p. 5233-5246.

Mathur, R., and Schlitt, W. J., 2010, Identification of the dominant Cu ore minerals providing soluble copper at Canariaco, Peru through Cu isotope analyses of batch leach experiments: Hydrometallurgy, v. 101, p. 15-19.

Mathur, R., Titley, S., Barra, F., Brantley, S., Wilson, M., Phillips, A., Munizaga, F., Maksaev, V., Vervoort, J., and Hart, G., 2009, Exploration potential of Cu isotope fractionation in porphyry copper deposits: Journal of Geochemical Exploration, v. 102, p. 1-6.

Wall, A. J., Heaney, P. J., Mathur, R., Post, J. E., and Anonymous, 2006, Copper isotope fractionation during the oxidative phase transition of sulfide minerals, chalcocite to covellite, using time-resolved synchrotron X-ray diffraction: Abstracts with Programs—Geological Society of America, v. 38, p. 432.

(b) References for Example 2

Asael D, Matthews A, Bar-Matthews M, Halicz L (2007) Copper isotope fractionation in sedimentary copper mineralization (Timna Valley, Israel). Chem Geol 243:238-254

Asael D, Matthews A, Oszczepalski S, Bar-Matthews M, Halicz L (2009) Fluid speciation controls of low temperature copper isotope fractionation applied to the Kupferschiefer and Timna ore deposits. Chem Geol 262:147-158

Haest M, Muchez P, Petit J C J, Vanhaecke F (2009) Cu isotope ratio variations in the dikulushi cu-ag deposit, drc: of primary origin or induced by supergene reworking? Econ Geol 104:1055-1064

Kimball B E, Mathur R, Dohnalkova A C, Wall A J, Runkel R L, Brantley S L (2009) Copper isotope fractionation in acid mine drainage: Geochim Cosmochim Acta 73:1247-1263

Larson P B, Maher K, Ramos F C, Chang Z, Gaspar M, Meinert L D (2003) Copper isotope ratios in magmatic and hydrothermal ore-forming environments. Chem Geol 201:337-350

Maher K C, Larson P B (2007) Variation in Copper Isotope Ratios and Controls on Fractionation in Hypogene Skarn Mineralization at Coroccohuayco and Tintaya, Peru. Econ Geol 102:225-237

Mathur R, Ruiz J, Titley S, Liermann L, Buss H, Brantley S L (2005) Cu isotopic fractionation in the supergene environment with and without bacteria. Geochim Cosmochim Acta 69:5233-5246

Mathur R, Schlitt W J (2010) Identification of the dominant Cu ore minerals providing soluble copper at Canariaco, Peru through Cu isotope analyses of batch leach experiments. Hydrometallurgy 101:15-19

Mathur R, Titley S, Barra F, Brantley S, Wilson M, Phillips A, Munizaga F, Maksaev V, Vervoort J, Hart G (2009) Exploration potential of Cu isotope fractionation in porphyry copper deposits. J Geochem Explor 102:1-6

Wall A J, Heaney P J, Mathur R, Post J E, Anonymous (2006) Copper isotope fractionation during the oxidative phase transition of sulfide minerals, chalcocite to covellite, using time-resolved synchrotron X-ray diffraction. GSA Abstracts with Programs 38, p 432

(c) References for Example 3

Archer, C., Vance, D., 2004. Mass discrimination correction in multiple-collector plasma source mass spectrometry: an example using Cu and Zn isotopes. Journal of Analytical Atomic Spectrometry, 19: 656-665.

Balistrieri, L. S., Borrok, D. M., Wanty, R. B., Ridley, W. I., 2008. Fractionation of Cu and Zn isotopes during adsorption onto amorphous Fe(III) oxyhydroxide: Experimental mixing of acid rock drainage and ambient river water. Geochimica et Cosmochimica Acta, 72(2): 311-328.

Bermin, J., Vance, D., Archer, C., Statham, P. J., 2006. The determination of the isotopic composition of Cu and Zn in sea water. Chemical Geology, 226(3-4): 280-297.

Bigalke, M., Weyer, S., Kobza, J., Wilcke, W., 2010. Stable Cu and Zn isotope ratios as tracers of sources and transport of Cu and Zn in contaminated soil. Geochimica et Cosmochimica Acta, 74(23): 6801-6813.

Bigalke, M., Weyer, S., Wilcke, W., 2009. Stable Copper Isotopes: A Novel Tool to Trace Copper Behavior in Hydromorphic Soils. Soil Sci Soc Am J, 74(1): 60-73.

Bigalke, M., Weyer, S., Wilcke, W., 2011. Stable Cu isotope fractionation in soils during oxic weathering and podzolization. Geochimica et Cosmochimica Acta, 75(11): 3119-3134.

Borrok, D. M., Nimick, D. A., Wanty, R. B., Ridley, W. I., 2008. Isotopic variations of dissolved copper and zinc in stream waters affected by historical mining. Geochimica et Cosmochimica Acta, 72(2): 329-344.

Eppinger, R. G., Fey, D., L., Giles, S. A., Kelley, K. D., Smith, S. M., This volume. An exploration hydrogeochemical study at the Giant Pebble porphyry Cu—Au—Mo deposit, Alaska, USA, using high resolution ICP-MS. Economic Geology.

Fernandez, A., Borrok, D. M., Fractionation of Cu, Fe, and Zn Isotopes during the oxidative weathering of sulfide-rich rocks. Chemical Geology, In Press, Accepted Manuscript.

Graham, S., Pearson, N., Jackson, S., Griffin, W., O'Reilly, S. Y., 2004. Tracing Cu and Fe from source to porphyry; in situ determination of Cu and Fe isotope ratios in sulfides from the Grasberg Cu—Au deposit. Chemical Geology, 207(3-4): 147-169.

Gregory, M. J., Lang, J. R., Gilbert, S. & Hoal, K. O, This volume. Geometallurgy of the Pebble Porphyry Copper-Gold-Molybdenum Deposit, Alaska: Implications for Gold Distribution and Paragenesis. Economic Geology.

Haest, M., Muchez, P., Petit, J. C. J., Vanhaecke, F., 2009. Cu Isotope Ratio Variations In The Dikulushi Cu—Ag Deposit, Drc: Of Primary Origin Or Induced By Supergene Reworking? Economic Geology, 104(7): 1055-1064.

Ikehata, K., Notsu, K., Hirata, T., 2011. Copper Isotope Characteristics Of Copper-Rich Minerals From Besshi-Type Volcanogenic Massive Sulfide Deposits, Japan, Determined Using A Femtosecond LA-MC-ICP-MS. Economic Geology, 106(2): 307-316.

Kimball, B. E. et al., 2009. Copper isotope fractionation in acid mine drainage. Geochimica et Cosmochimica Acta, 73(5): 1247-1263.

Lang, J. R., Gregory, M. J., Rebagliati, C. M., Payne, J. G, Oliver, J. L., & Roberts, K., This volume. Geology and Magmatic-Hydrothermal Evolution of the Giant Pebble Porphyry Copper-Gold-Molybdenum Deposit, Southwest Alaska, USA. Economic Geology.

Li, W., Jackson, S. E., Pearson, N. J., Alard, O., Chappell, B. W., 2009. The Cu isotopic signature of granites from the Lachlan Fold Belt, SE Australia. Chemical Geology, 258(1-2): 38-49.

Li, W., Jackson, S. E., Pearson, N. J., Graham, S., 2010. Copper isotopic zonation in the Northparkes porphyry Cu—Au deposit, SE Australia. Geochimica et Cosmochimica Acta, 74(14): 4078-4096.

Maher, K. C., Jackson, S., Mountain, B., 2011. Experimental evaluation of the fluid mineral fractionation of Cu isotopes at 250° C. and 300° C. Chemical Geology, 286(3-4): 229-239.

Maher, K. C., Larson, P. B., 2007. Variation in Copper Isotope Ratios and Controls on Fractionation in Hypogene Skarn Mineralization at Coroccohuayco and Tintaya, Peru. Economic Geology, 102(2): 225-237.

Marechal, C. N., Telouk, P., Albarede, F., 1999. Precise analysis of copper and zinc isotopic compositions by plasma-source mass spectrometry. Chemical Geology, 156(1-4): 251-273.

Mathur, R., Dendas, M., Titley, S., Phillips, A., 2010. Patterns in the Copper Isotope Composition. of Minerals in Porphyry Copper Deposits in Southwestern United States. Economic Geology, 105(8): 1457-1467.

Mathur, R. et al., 2005. Cu isotopic fractionation in the supergene environment with and without bacteria. Geochimica et Cosmochimica Acta, 69(22): 5233-5246.

Mathur, R., Schlitt, W. J., 2010. Identification of the dominant Cu ore minerals providing soluble copper at Cañariaco, Peru through Cu isotope analyses of batch leach experiments. Hydrometallurgy, 101(1-2): 15-19.

Mathur, R. et al., 2009. Exploration potential of Cu isotope fractionation in porphyry copper deposits. Journal of Geochemical Exploration, 102(1): 1-6.

Mirnejad, H., Mathur, R., Einali, M., Dendas, M., Alirezaei, S., 2010. A comparative copper isotope study of porphyry copper deposits in Iran. Geochemistry—Exploration, Environment, Analysis, 10(4): 413-418.

Palacios, C., Rouxel, O., Reich, M., Cameron, E., Leybourne, M., 2011. Pleistocene recycling of copper at a porphyry system, Atacama Desert, Chile: Cu isotope evidence. Mineralium Deposita, 46(1): 1-7.

Pokrovsky, O. S., Viers, J., Emnova, E. E., Kompantseva, E. I., Freydier, R., 2008. Copper isotope fractionation during its interaction with soil and aquatic microorganisms and metal oxy(hydr)oxides; possible structural control. Geochimica et Cosmochimica Acta, 72(7): 1742-1757.

Pribil, M. J., Wanty, R. B., Ridley, W. I., Borrok, D. M., Influence of sulfur-bearing polyatomic species on high precision measurements of Cu isotopic composition. Chemical Geology, 272(1-4): 49-54.

Seo, J. H., Lee, S. K., Lee, I., 2007. Quantum chemical calculations of equilibrium copper (I) isotope fractionations in ore-forming fluids. Chemical Geology, 243(3-4): 225-237.

Vance, D. et al., 2008. The copper isotope geochemistry of rivers and the oceans. Earth and Planetary Science Letters, 274(1-2): 204-213.

Wall, A. J. et al., 2011a. A flow-through reaction cell that couples time-resolved X-ray diffraction with stable isotope analysis. Journal of Applied Crystallography, 44(2): 429-432.

Wall, A. J., Mathur, R., Post, J. E., Heaney, P. J., 2011b. Cu isotope fractionation during bornite dissolution: An in situ X-ray diffraction analysis. Ore Geology Reviews, 42(1): 62-70.

Zhu, X. K. et al., 2002. Mass fractionation processes of transition metal isotopes. Earth and Planetary Science Letters, 200(1-2): 47-62.

Zhu, X. K., O'Nions, R. K., Guo, Y., Belshaw, N. S., Rickard, D., 2000. Determination of natural Cu-isotope variation by plasma-source mass spectrometry; implications for use as geochemical tracers. Chemical Geology, 163(1-4): 139-149.

What is claimed is:

1. A method comprising performing mining activities within an area of interest where mining activities have not been previously performed, wherein the area of interest is identified as having a subsurface copper ore present by determining an enriched $\delta^{65}Cu‰$ signature relative to a δ65Cu‰ signature in NIST 976 in a natural water sample collected without core drilling, wherein the area of interest is at most 25 km² surrounding where the natural water sample was collected, wherein the mining activities comprise one or more of geophysical surveying, soil sampling, rock core drilling, and extracting copper ore.

2. The method of claim 1, wherein the determining is performed by a mass spectrometer.

3. The method of claim 1, wherein the enriched $\delta^{65}Cu‰$ signature is determined when $\delta^{65}Cu‰$ is above 1.5‰ relative to the $\delta^{65}Cu‰$ signature in NIST 976, which indicates that the subsurface copper ore is a hypogene zone.

4. The method of claim 1, wherein the enriched $\delta^{65}Cu‰$ signature is determined when $\delta^{65}Cu‰$ is above 0.5‰ relative to the $\delta^{65}Cu‰$ signature in NIST 976.

5. The method of claim 1, wherein the enriched $\delta^{65}Cu‰$ signature is determined by an average $\delta^{65}Cu‰$ value.

6. The method of claim 1, wherein the natural water is seep water.

7. The method of claim 1, wherein performing mining activities is extracting copper ore.

8. The method of claim 1, wherein performing mining activities is geophysical surveying.

9. The method of claim 1, wherein performing mining activities is rock core drilling.

10. The method of claim 1, wherein performing mining activities is soil sampling.

11. The method of claim 1, wherein the area of interest is at most 10 km².

12. The method of claim 1, wherein the enriched $\delta^{65}Cu‰$ signature is determined when $\delta^{65}Cu‰$ is above 1.0‰ relative to the $\delta^{65}Cu‰$ signature in NIST 976.

13. The method of claim 1, wherein the enriched $\delta^{65}Cu‰$ signature is determined when $\delta^{65}Cu‰$ is above 1.5‰ relative to the $\delta^{65}Cu‰$ signature in NIST 976.

14. The method of claim 1, wherein the enriched $\delta^{65}Cu‰$ signature is determined when $\delta^{65}Cu‰$ is above 2.0‰ relative to the $\delta^{65}Cu‰$ signature in NIST 976.

15. The method of claim 1, wherein the enriched $\delta^{65}Cu‰$ signature is determined when $\delta^{65}Cu‰$ is above 2.5‰ relative to the $\delta^{65}Cu‰$ signature in NIST 976.

16. A method comprising identifying a subsurface copper ore within an area of interest by determining an enriched $\delta^{65}Cu‰$ signature relative to a $\delta^{65}Cu‰$ signature in NIST 976 in a natural water sample collected without core drilling and surrounded by the area of interest being at most 25 km² from where the natural water sample was collected wherein mining activities have not been previously performed.

17. The method of claim 16, wherein identifying comprises reporting that the enriched $\delta^{65}Cu‰$ signature is a $\delta^{65}Cu‰$ of at least 0.5‰ relative to the $\delta^{65}Cu‰$ signature in NIST 976.

18. The method of claim 16, wherein the area of interest is at most 10 km².

19. The method of claim 16, wherein identifying comprises reporting that the enriched $\delta^{65}Cu‰$ signature is a $\delta^{65}Cu‰$ of at least 1.0‰ relative to the $\delta^{65}Cu‰$ signature in NIST 976.

20. The method of claim 16, wherein identifying comprises reporting that the enriched $\delta^{65}Cu‰$ signature is a $\delta^{65}Cu‰$ of at least 1.5‰ relative to the $\delta^{65}Cu‰$ signature in NIST 976.

* * * * *